United States Patent [19]

Takada et al.

[11] Patent Number: 5,461,062
[45] Date of Patent: Oct. 24, 1995

[54] CONDENSED IMIDAZOPYRIDINE DERIVATIVES

[75] Inventors: Susumu Takada, Kawanishi; Takashi Sasatani, Nara; Nobuo Chomei, Sakai; Makoto Adachi, Ikoma; Akira Matsushita, Kobe, all of Japan

[73] Assignee: Shionogi & Co., Ltd., Osaka, Japan

[21] Appl. No.: 297,885

[22] Filed: Aug. 30, 1994

Related U.S. Application Data

[62] Division of Ser. No. 12,424, Feb. 2, 1993, Pat. No. 5,378,348.

[30] Foreign Application Priority Data

Feb. 12, 1992 [JP] Japan ................................. 4-59347

[51] Int. Cl.⁶ ........................ A61K 31/44; C07D 471/04
[52] U.S. Cl. .................................. 514/293; 546/82
[58] Field of Search ................................ 546/82; 514/293

[56] References Cited

FOREIGN PATENT DOCUMENTS 0168350  1/1986  European Pat. Off. .
0223420  5/1987  European Pat. Off. .

*Primary Examiner*—Raymond Henley, III
*Assistant Examiner*—Phyllis G. Spivack
*Attorney, Agent, or Firm*—Wenderoth, Lind & Ponack

[57]  ABSTRACT

A compound of the formula:

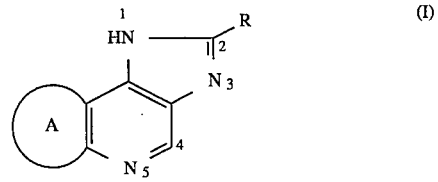

wherein R is an optionally substituted phenyl group, 5-membered; the A ring is a 5 to 7 membered alicyclic group in which said A ring may have an alkyl group as a substituent, or a pharmaceutically acceptable salt thereof, and is useful as a psychotropic agent.

5 Claims, No Drawings

CONDENSED IMIDAZOPYRIDINE DERIVATIVES

This application is a division of application Ser. No. 08/012,424, filed Feb. 2, 1993 (now U.S. Pat. No. 5,378,348).

The present invention relates to novel condensed imidazopyridine derivatives having high affinity to benzodiazepine receptor, and, useful as psychotropic agents such as an antianxiety agent, anesthesia antagonistic agent and cerebral function activator.

Benzodiazepine (BDZ) derivatives represented by diazepam have been used as an antianxiety agent for a long time. According to the recent pharmacological studies, it has been found that a receptor showing an affinity specific to BDZ derivatives exists in the central nervous system. Then, as the results of extended studies, there have been developed BDZ agonists which are structurally different from BDZ but show high affinity to BDZ receptor and BDZ-like activity, BDZ inverse agonists which show high affinity to BDZ receptor but show a reversed action to BDZ, and BDZ antagonists which show high affinity to BDZ receptor but show no pharmacological activity and exhibit antagonistic action to the BDZ agonists or inverse agonists. On the other hand, various non-BDZ compounds are nowadays studied, and imidazopyridine derivatives disclosed in Japanese Patent Publication (Kokai) Sho 63-99069 and pyrazolopyridine derivatives disclosed in U.S. Pat. No. 4,826,854 and U.S. Pat. No. 4,740,512 are reported to show high affinity to BDZ receptor and useful as psychotropic agents.

However, said BDZ derivatives show sometimes various side effects such as dizziness, sleepiness or the like. On the other hand, non-BDZ compounds nowadays under development have also drawbacks such as poor solubility and absorption. Accordingly, there has been a strong desire for development of novel non-BDZ compounds which are free of said drawbacks.

As the result of extensive study, the present inventors have found that the compounds of the following formula (I):

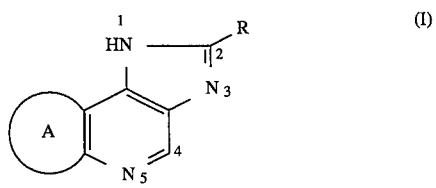

wherein R represents an optionally substituted aryl group or an optionally substituted aromatic heterocyclic group; A ring represents 5 to 9 membered alicyclic group, in which one or more of carbon atoms constituting said A ring may be replaced by O, S, SO, $SO_2$ and/or $NR^1$ (in which $R^1$ means hydrogen, alkyl, alkoxycarbonyl, carbamoyl or acyl group) and/or said A ring may have alkyl group as a substituent, or its salts, can meet the above-mentioned requirements. The present invention is based on this finding.

The compounds of the present invention represented by the formula (I) exhibit either of agonistic activity, inverse agonistic activity, and antagonistic activity after binding to BDZ receptor. Those having agonistic activity are expected to be useful as sleep inducers or antianxiety agents, those having antagonistic activity useful as anesthesia antagonists, and those having inverse agonistic activity useful as cerebral function activators.

In the present specification, the aryl group includes phenyl, naphthyl, anthryl, phenanthryl, and the like. These groups may have one or more substituents selected from alkyl, hydroxy, alkoxy, aryloxy, acyloxy (e.g. alkanoyloxy, aroyloxy, etc.), carboxy, ester (e.g. alkoxycarbonyl, aralkoxycarbonyl, etc.), cyano, amino, mono- or di-(substituted)amino, hydrazino, hydroxyamino, alkoxyamino, halogen, nitro, formyl, acyl (e.g. alkanoyl, aroyl, etc.), (thio)carbamoyl, (thio)carbomoyloxy, (thio) ureido, sulfonamide, mono- or di-(substituted)-sulfonamide, sulfonic acid, halogenoalkyl, hydroxyalkyl, alkoxyalkyl, acyloxyalkyl, nitroalkyl, (acyl)aminoalkyl, cyanoalkyl, carboxyalkyl and the like. Preferred are phenyl optionally substituted by one or more substituents selected from methyl, methoxy, chlorine and the like.

The aromatic heterocyclic group means a 5 to 6 membered carbon ring containing one or more atoms or groups selected from oxygen, sulfur or nitrogen atom within the ring and may be optionally condensed with a carbon ring or other heterocyclic ring.

Examples of said aromatic heterocyclic rings are pyrrolyl, indolyl, carbazolyl, imidazolyl, pyrazolyl, benzimidazolyl, pyridyl, quinolyl, isoquinolyl, pyridazinyl, pyrimidinyl, pyrazinyl, cinnolyl, phthaladinyl, quinazolinyl, naphthylidinyl, quinoxalinyl, phenadinyl, 1,3,5-triazinyl, 1,2,4-triazinyl, 1,2,3-triazinyl, isoxazolyl, benzisoxazolyl, oxazolyl, benzoxazolyl, 1,2,3-oxadiazolyl, 1,2,4-oxadiazolyl, 1,2,5-oxadiazolyl, 1,3,4-oxadiazolyl, benzoxadiazolyl, isothiazolyl, benzisothiazolyl, thiazolyl, benzthiazolyl, 1,2,3-thiadiazolyl, 1,2,4-thiadiazolyl, 1,2,5-thiadiazolyl, 1,3,4-thiadiazolyl, benzthiadiazolyl, furyl, benzfuryl, thienyl, benzthienyl, and the like. Further, these cyclic groups may optionally have one or more substituents selected from the group consisting of alkyl, hydroxy, alkoxy, carboxy, ester (e.g. alkoxycarbonyl, aralkoxycarbonyl, etc.), cyano, amino, mono- or di-(substituted)amino, hydrazino, hydroxyamino, alkoxyamino, halogen, nitro, formyl, acyl (e.g. alkanoyl, aroyl, etc.) (thio)carbamoyl, (thio)carbamoyloxy, (thio)ureido, sulfonamide, mono- or di-(substituted)sulfonamide, sulfonic acid, halogenoalkyl, hydroxyalkyl, alkoxyalkyl, acyloxyalkyl, nitroalkyl, (acyl)aminoalkyl, cyanoalkyl, carboxyalkyl and the like. Preferred are thienyl, furyl, isoxazolyl and pyridyl optionally substituted by methyl or the like.

The 5 to 9 membered alicyclic group is condensed with the adjacent pyridine ring. Specific examples of the alicyclic group include cyclopenteno ring, cyclohexeno ring, cyclohepteno ring, cycloocteno ring and cyclononeno ring, and 5 to 7 membered alicyclic ring is preferred. Further, one or more of carbon atoms constituting said alicyclic ring may be replaced by O, S, SO, $SO_2$ and/or $NR^1$ (in which $R^1$ has the same significance as defined above). Such alicyclic ring containing hetero atoms includes pyrrolidino, pyrrolino, imidazolidino, imidazolino, pyrazolidino, dihydrothiopheno, dihydrofurano, thiazolino, dihydropyrano, dihydrothiopyrano, piperidino, piperazino, morpholino, thiomorpholino, tetrahydropyridino and tetrahydropyrimidino. Preferred groups are dihydropyrano, dihydrothiopyrano and piperidino. Further, said alicyclic group may have an alkyl group as a substituent, and 1 to 2 methyl or ethyl groups are preferred.

The term "alkyl" generally means a straight or branched alkyl having 1 to 10 carbon atoms, and lower alkyl having 1 to 6 carbon atoms are preferred. It illustratively includes methyl, ethyl, n-propyl, isopropyl, n-butyl, isobutyl, sec-butyl, tert-butyl, n-pentyl, isopentyl, neopentyl, tert-pentyl, 2-methylbutyl, n-hexyl and isohexyl.

The alkoxycarbonyl illustratively includes methoxycarbonyl group, ethoxycarbonyl group, tert-butoxycarbonyl and benzyloxycarbonyl group, and ethoxycarbonyl group is particularly preferred.

The acyl group means aromatic acyl and aliphatic acyl groups. The aromatic acyl group includes benzoyl, 4-nitrobenzoyl, 4-tert-butylbenzoyl, benzenesulfonyl, toluenesulfonyl, and the like, and the aliphatic acyl group includes formyl, acetyl, propionyl, butyryl, valeryl groups. Above all, acetyl is preferred as aliphatic acyl group.

Three tautomers can exist with respect to the compounds of the present invention, and the following formula (I) is just shown as its representative example. Thus, the compounds of the present invention include other tautomers, namely compounds (I') having a double bond in (1–2, 3a–3b and 4–5 positions) and compounds (I'') having a double bond in (1–3b, 2–3 and 3a–4 positions).

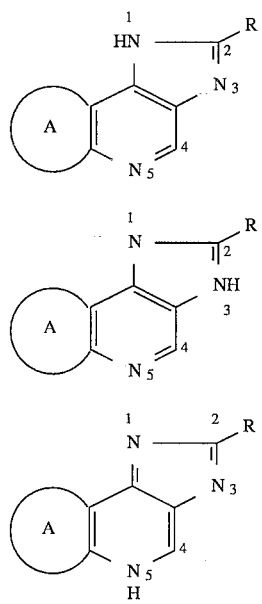

The compounds of the present invention include all the pharmaceutically acceptable salts of the compounds (I). In general, they can form a salt with inorganic acids, organic acids or acidic amino acids. The inorganic acids include hydrochloric acid, hydrobromic acid, sulfuric acid, phosphoric acid, orthophosphoric acid, and the like. The organic acids include formic acid, acetic acid, trifluoroacetic acid, oxalic acid, tartaric acid, fumaric acid, maleic acid, methanesulfonic acid, benzenesulfonic acid, p-toluenesulfonic acid, and the like. The acidic amino acids include ornithine, aspartic acid, glutamic acid and the like. In particular, preferable are salts with an inorganic acid (e.g. hydrochloric acid), phosphoric acid and orthophosphoric acid.

Typical process for the preparation of the compounds of the present invention is shown below.

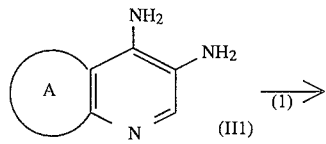

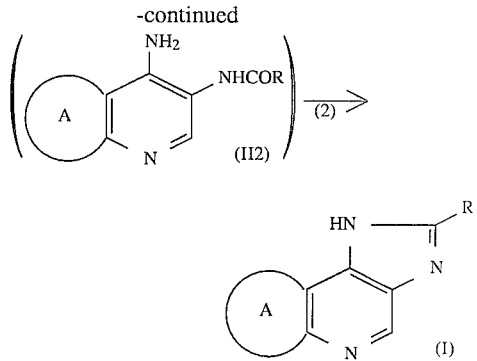

In the above formulae, R and A each have the same significance as defined above.

First Step (Acylation)

This reaction is generally effected by reacting a compound (II1) with an acylating agent corresponding to the desired acyl group in an appropriate solvent. The reaction is carried out at temperature from −10° to 50° C., preferably 0° C. to around room temperature for 10 minutes to 5 hours, preferably for 30 minutes or 1 hour.

The solvent to be used includes triethylamine, pyridine, benzene, toluene, ether, methylene chloride, tetrahydrofuran, acetonitrile, dimethylformamide, chloroform, hexamethyltriamide, hexamethylphosphoric triamide, and a mixture thereof.

The acylating agent includes an acyl halide (e.g. benzoyl chloride), isoxazolyl chloride and a mixture of carboxylic acid and thionyl chloride. A condensing agent such as DCC, polyphosphoric acid or the like may be used together.

Second Step (Cyclization)

The resultant compound (II2) can be used for the present step with or without isolation. The compound (I) can be obtained by heating the compound (II2) in an appropriate solvent at temperature from about 50° to 400° C., preferably 100° to 250° C. for 30 minutes to 10 hours, preferably for 1 to 5 hours.

This reaction is accelerated by neutralizing with a base, and the reaction is effected at comparatively low temperature, namely 50° to 200° C., preferably 100° to 150° C. on an oil bath in the presence of a ring-closing agent.

As the solvent used herein there are exemplified an alcohol solvent such as diethylene glycol, triethylene glycol or the like and an ethereal solvent such as 2-methoxyethyl ether or the like.

The base includes sodium hydrogencarbonate, potassium hydroxide, sodium carbonate, sodium acetate, triethylamine and pyridine.

The ring-closing agent includes polyphosphoric acid, polyphosphoric acid ester, sulfuric acid, acetic acid, phosphorus pentoxide and the like.

Where the resultant compound (I) has NR$^{1'}$ on the ring A (wherein R$^{1'}$ means alkoxycarbonyl group), it can be subjected to the following step, if necessary.

(a) R$^1$: Hydrogen

The product can be obtained by subjecting the resultant alkoxycarbonyl compound to hydrolysis preferably in the presence of a catalyst in an appropriate solvent in a conventional manner.

The reaction is carried out at temperature from room temperature to 200° C., preferably 50° to 80° C., for 1 to 20 hours, preferably 4 to 6 hours.

The catalyst includes hydrobromic acid, hydrochloric acid, sulfuric acid, sodium hydroxide and potassium hydroxide.

The appropriate solvent includes acetic acid, methanol, ethanol, acetonitrile, and a mixture thereof. These solvents are used preferably in hydrous conditions.

(b) $R^1$: Acyl group

The compound obtained in Step (a) is subjected to acylation with an acylating agent such as acetic anhydride or acetyl chloride in a conventional manner, preferably in the presence of a base.

The reaction is carried out at temperature from 0° to 100° C., preferably 10° to 30° C., for 30 minutes to 5 hours, preferably 1 to 3 hours.

The base includes pyridine, triethylamine, 4-dimethylaminopyridine, and the like.

(c) $R^1$: Alkyl group

The product can be obtained by subjecting the alkoxycarbonyl compound to reduction, preferably in the presence of a reducing agent in an appropriate organic solvent.

The appropriate solvent includes tetrahydrofuran, diethyl ether and dimethoxyethane.

Any reducing agent ordinarily usable for the reduction can be used herein, and preferable examples of the reducing agent are lithium aluminum hydride, sodium bis(2-methoxyethoxy)aluminum hydride, diisobutylaluminum hydride, sodium borohydride and lithium borohydride.

The compound (II1) usable as a starting material in said preparation can be synthesized in the following Process A and Process B. Further, the compound (II2) can be directly prepared according to Process C.

Process A

Synthetic Process of (II1)

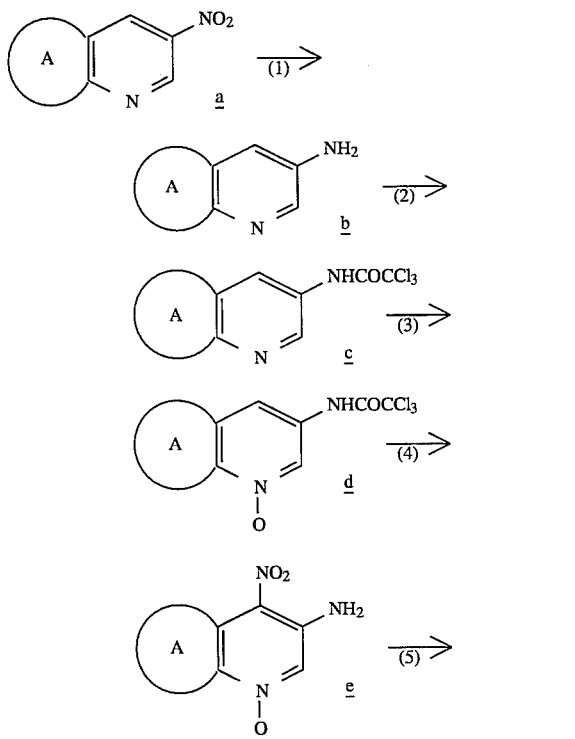

(1) Compound b can be prepared by subjecting Compound a to hydrogenation.

This hydrogenation is carried out by using a hydrogenating catalyst in an appropriate inert solvent at temperature from 10° to 50° C. preferably around room temperature for 30 minutes to 10 hours, preferably 5 to 7 hours.

The inert solvent usable herein includes water, acetic acid, methanol, ethanol, dioxane, and the like.

The hydrogenating catalyst includes platinum, palladium-carbon, radium-carbon, Raney nickel, and the like.

(2) Compound c can be prepared by reacting Compound b with trichloroacetyl chloride in an appropriate solvent, preferably in the presence of a base.

The appropriate solvent illustratively includes a halogenohydrocarbon (e.g. methylene chloride, chloroform, etc.) and an ether (e.g. tetrahydrofuran, dioxane, diethyl ether, diethyl ether, isopropyl ether, etc.).

The base includes triethylamine, sodium hydrogencarbonate, potassium hydroxide, sodium carbonate, sodium acetate, pyridine and the like.

The reaction is effected at a temperature from 0° to 80° C., preferably around room temperature, for 10 minutes to 5 hours, preferably 20 minutes to 2 hours.

(3) Compound d can be prepared by oxidizing Compound c. Thus, the reaction is effected by reacting Compound c with m-chloroperbenzoic acid under mild conditions in a nonpolar solvent or by reacting Compound c with hydrogen peroxide in an acidic solvent such as acetic acid or the like.

The nonpolar solvent includes methylene chloride, benzene, chloroform, hexane, and carbon tetrachloride.

(4) Compound e can be prepared by nitrating Compound d and deprotecting the resulting compound.

The nitration is carried out by the use of fuming nitric acid or nitric acid, preferably in the presence of an acidic solvent, preferably sulfuric acid or the like, at a temperature from 10° to 200° C., preferably 30° to about 80° C. over a period of 1 to 10 hours, preferably 3 to 6 hours. Higher temperature may be required when nitric acid is used.

Deprotection is carried out in a conventional manner, for example, by treating with alkaline medium such as aqueous ammonia or sodium hydroxide.

(5) Compound (II1) can be prepared by hydrogenating Compound e by the use of a hydrogenating catalyst in an appropriate inert solvent at temperature from 10° to 50° C., preferably around room temperature over a period of 30 minutes to 10 hours, preferably 5 to 7 hours.

The inert solvent includes water, acetic acid, methanol, ethanol, dioxane, and the like.

The hydrogenating catalyst includes Raney nickel, Platinum-carbon, palladium-carbon, radium-carbon, and the like, and in particular, Raney nickel is preferred.

Process B

Synthetic Process of (II1)

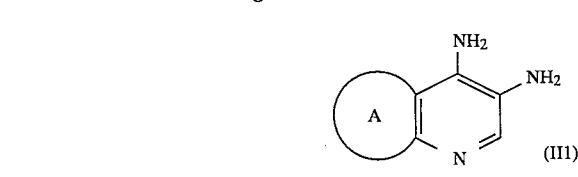

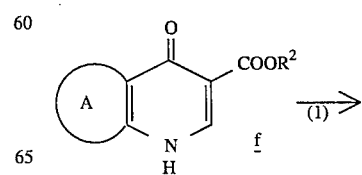

In the above formulae, A has the same significance as previously defined.

-continued

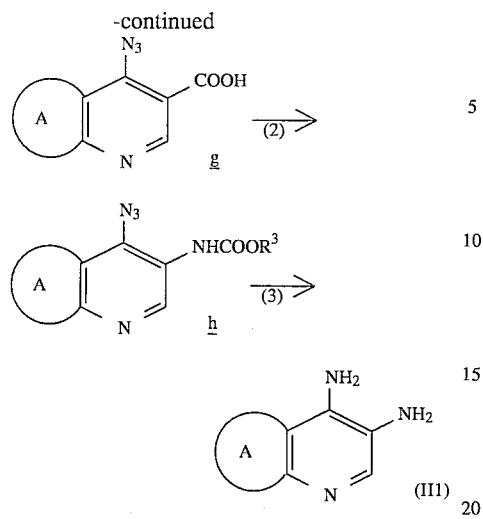

In the above formulae, $R^2$ and $R^3$ each mean lower alkyl group, and A has the same significance as previously defined.

(1) Compound f is allowed to react with phosphorus trichloride, phosphorous pentachloride, or phosphorus oxychloride (e.g. metaphosphoryl chloride) to give the 3-chloro compound. Then, the 3-azido compound g is obtained by treating the 3-chloro compound with a metal azide such as sodium azide, lead azide, ferrous azide or the like.

(2) Compound g is allowed to react with ethyl chloroformate, preferably in the presence of a base, in an appropriate solvent to give an acid anhydride. The, the acid anhydride is allowed to react with a metal azide to give an azide carbonyl, $CON_3$, which is refluxed with an appropriate alcohol to give Compound h.

The solvent for the reaction includes tetrahydrofuran, dioxane, diethyl ether, toluene, acetonitrile, and the like.

The base to be used is triethylamine, sodium bicarbonate, potassium hydroxide, sodium carbonate, pyridine, and the like.

The alcohol includes alcohols having a branched alkyl chain such as isopropanol, tert-butanol, and the like.

(3) Compound h is subjected to reduction in a conventional manner and then deacylated at the 3 position to give Compound (II1).

All the reducing agents ordinarily used for reduction can be used herein, and stannous chloride hydrate is most preferred for this reaction.

Process C

Synthetic Process of (II2)

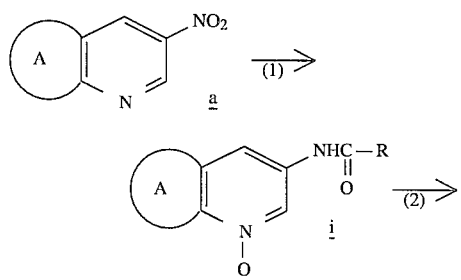

-continued

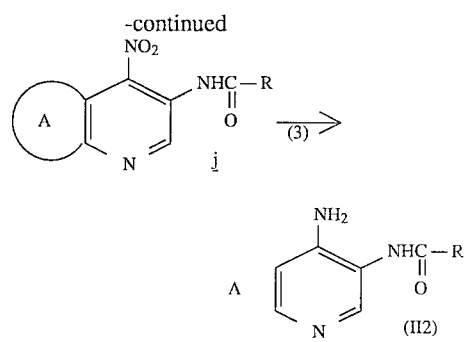

In the above formulae, A and R have the same significance as previously defined.

(1) Compound i is obtained by subjecting Compound a to oxidation, and then reduction, and reacting the resulting amino/oxide with an acylating agent.

Oxidation can be carried out in the same manner as in Process A (3) for the production of Compound (II1).

Reduction can be carried out in the same manner as in Process A (1) for the production of Compound (II1).

The acylating agent includes various agents containing desired acyl group and illustratively includes a chloride (e.g. isoxazolyl chloride), aroyl chloride (e.g. benzoyl chloride), acid chloride, acid anhydride, a combination of carboxylic acid and thionyl chloride, and the like.

(2) Compound i is nitrated with fuming nitric acid, and the resulting nitrated oxide is subjected to ordinary deoxygenation in the presence of a tertiary phosphine type deoxygenating reducing agent such as phosphorus tribromide, phosphorus trichloride or triphenylphosphine to give Compound j.

(3) Compound (II2) is obtained by reducing Compound j.

Reduction is carried out in the same manner as in Process A (1) for the production of Compound (II1).

Further, the compounds of the present invention can be prepared by adopting the alternative process as shown in the following Reaction Scheme 2.

Reaction Scheme 2

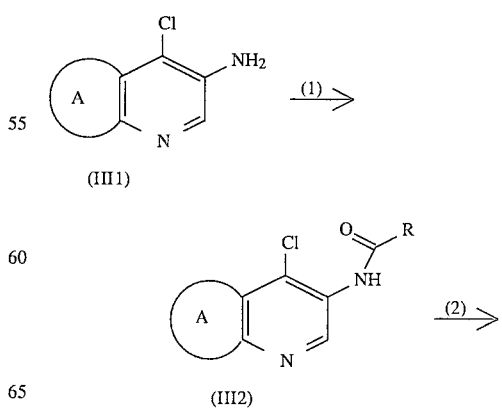

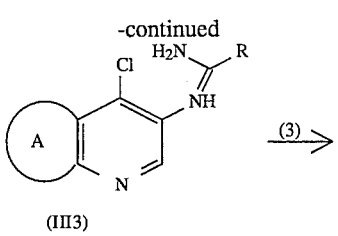

(III3)

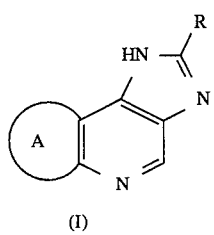

(I)

In the above formulae, R and A each have the same significance as previously defined.

First Step

This step includes a process for preparing Compound (III2) which comprises acylating Compound (III1) with an acyl halide of the formula R—COCl. This reaction is generally carried out at temperature from −20° to 60° C., preferably at from −10° to 10° C. for a period of several minutes to several hours. As a solvent, there can be used methylene chloride, dimethylformamide, chloroform, tetrahydrofuran, and the like.

Second Step

This step includes a process for preparing Compound (III3) which comprises reacting Compound (III2) with a chlorinating agent and subsequently with ammonia. In general, the reaction is carried out using a chlorinating agent such as phosphorus pentachloride and phosphorus oxychloride, and a base such as pyridine and triethylamine at temperature from 0° to 60° C., preferably from 30° to 50° C. over a period of several minutes to several hours, and then treating the resulting product with ammonia. As a solvent, there can be employed methylene chloride, chloroform, tetrahydrofuran, and the like.

Third Step

Compound (I) is obtained by subjecting Compound (III3) to cyclization under heating. As a solvent there can be used an inert solvent having a high boiling point, such as N-methyl-2-pyrrolidone, a mixture of biphenylether and biphenyl, and the like. The reaction is ordinarily carried out at a temperature from 50° to 250° C. over a period of several minutes to several hours.

The starting materials used in the above-mentioned alternative process as shown in Reaction Scheme 2 can be prepared by methods hereinafter described in Reference Example 5.

The compounds of the present invention can be orally or parenterally administered. For oral administration, the compounds of the present invention can be formulated in conventional formulations, for example, solid forms such as tablets, powders, granules, capsules or the like; liquid forms such as solutions; oil suspensions; or syrups or elixirs. For parenteral administration, the compounds of the present invention can be formulated in aqueous or oily suspended injections. The formulations may contain ordinary disintegrators, binders, lubricants, aqueous solvents, oily solvents, emulsifiers, suspenders or the like. Other adjuvants such as preservatives, stabilizers or the like, may be included therein.

Appropriate dosage of the compounds of the present invention vary depending upon administering routes, ages, body weights, conditions of particular patient and kinds of the diseases. In general, appropriate daily dosage for oral route is 0.05 to 500 mg, preferably 0.1 to 200 mg, and appropriate daily dosage for parenteral route is 0.01 to 300 mg, preferably 0.05 to 100 mg. The dosage may be administered after divided to two to five portions.

The following working examples will explain the present invention in more detail, but the scope of the present invention should not be limited thereto. The production of the compounds of the present invention based on Reaction Scheme 1 is illustrated by Examples 1 to 36, and the production of the compounds based on Reaction Scheme 2 is illustrated by Examples 37 to 44, respectively.

The abbreviations used in the Examples have the following meanings.

Me: Methyl

Et: Ethyl iPr: Isopropyl t-Bu: tert-Butyl

DMSO: Dimethyl sulfoxide

EXAMPLE 1

2-Phenyl-6,7,8,9-tetrahydro-1H-imidazo[4,5-c]quinoline (Ia-1)

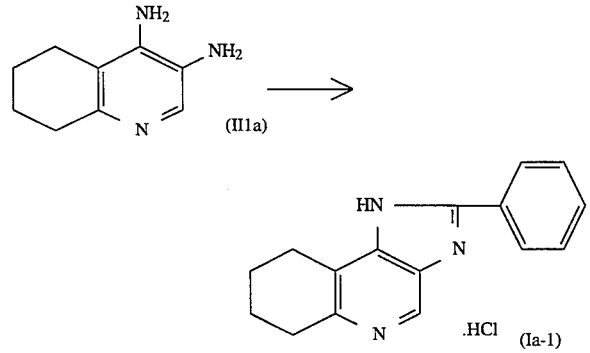

To a solution of 400 mg of 3,4-diamino-5,6,7,8-tetrahydroquinoline (IIIa) (synthesized in Reference Example 1 below) in 5 ml of pyridine is added 380 mg of benzoyl chloride with ice cooling, and the resultant mixture is stirred at room temperature for 30 minutes. The mixture is admixed with 261 mg of sodium acetate and 8 ml of ethylene glycol, and the mixture is heated at 150° C. (oil bath temperature) for 3.5 hours. After the mixture is concentrated in vacuo to remove the solvent, the residue is chromatographed on a silica gel column, and the purified product is mixed with conc hydrochloric acid to give the hydrochloride as crude crystals. The crude product is recrystallized from methanol-isopropanol to give 595 mg of the titled product (Ia-1) as colorless crystals melting at 292° to 299° C. Yield: 85% Elemental Analysis (%) $C_{16}H_{16}N_3Cl$ Calculated: C, 67.24; H, 5.64; N, 14.70; Cl, 12.41 Found: C, 67.11; H, 5,83; N, 14.63; Cl, 12.33 NMR ($d_6$-DMSO) δ:1.82 (4H, br.s); 2.64 (2H, br.s); 2.73 (2H, br.s); 7.23 to 7.40 (5H, m); 8.30 (1H, s)

EXAMPLES 2 to 6

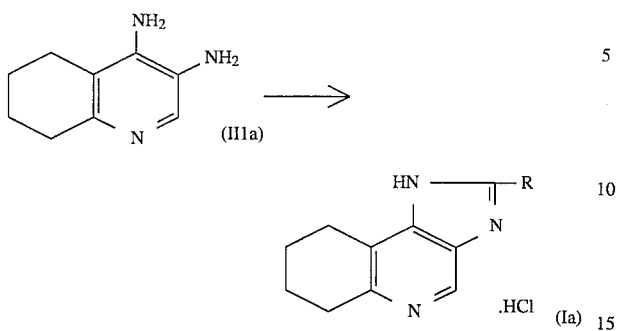

The following compounds are obtained by the use of Compound (IIIa) as a starting compound in the same manner as in Example 1.

Ia-2 (R=4-chlorophenyl): (Example 2) mp.: 312° to 319° C. (dec.) NMR ($D_2O$) δ: 1.91 (4H, m); 2.68 (2H, m); 2.95 (2H, m); 6.83 (2H, m); 7.19 (2H, m); 8.37 (1H, s)

Ia-3 (R=2-thienyl): (Example 3) mp.: 334° to 337° C. (dec.) NMR ($D_2O$) δ: 1.86 (4H, m); 2.70 (2H, m); 2.78 (2H, m); 7.03 (1H, m); 7.34 (1H, m); 7.64 (1H, m); 8.30 (1H, s)

Ia-4 (R=3-thienyl): (Example 4) mp.: 331° to 334° C. (dec.) NMR ($D_2O$) δ: 1.88 (4H, m); 2.76 (4H, m); 7.13 (1H, m); 7.47 (1H, m); 7.79 (1H, m); 8.35 (1H, s)

Ia-5 (R=2-furyl): (Example 5) mp.: 288° to 292° C. (dec.) NMR ($D_2O$) δ: 1.92 (4H, m); 2.78 (2H, m); 2.85 (2H, m); 6.69 (1H, m); 7.03 (1H, m); 7.75 (1H, m); 8.51 (1H, s)

Ia-6 (R=3-methyl-5-isoxazolyl): (Example 6) mp.: 272° to 280° C. (dec.) NMR (DMSO) δ: 1.91 (4H, br.s); 2.41 (3H, s); 3.11 (4H, br.s); 3.42 (1H, br.s, NH); 7.57 (1H, s); 9.29 (1H, s)

EXAMPLES 7 to 12

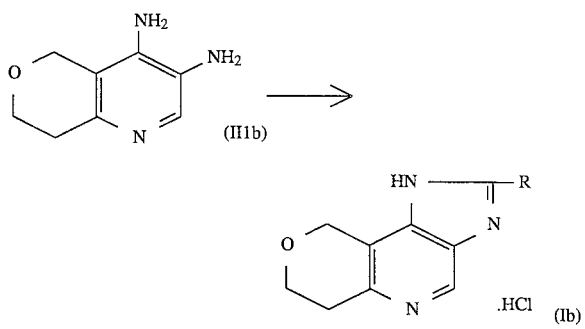

The following compounds are obtained by the use of Compound (IIIb) as a starting compound in the same manner as in Example 1.

Ib-1 (R=4-chlorophenyl): (Example 7) mp.: 291° to 297° C. (dec.) NMR ($D_2O$) δ: 3.17 (2H, m); 4.20 (2H, m); 4.86 (2H, s); 6.99 (2H, d); 7.34 (2H, d); 8.63 (1H, s)

Ib-2 (R=2-thienyl): (Example 8) mp.: 285° to 288° C. (dec.) NMR (DMSO) δ: 3.16 (2H, t); 3.40 (1H, br.s); 4.08 (2H, t); 5.12 (2H, s); 7.34 (1H, m); 7.97 (1H, m); 8.39 (1H, m); 9.16 (1H, s)

Ib-3 (R: 3-thienyl): (Example 9) mp.: 300° to 306° C. (dec.) NMR ($D_2O$) δ: 3.06 (2H, t); 4.16 (2H, t); 4.92 (2H, s); 7.28 (1H, m); 7.51 (1H, m); 7.95 (1H, m); 8.63 (1H, s)

Ib-4 (R=2-furyl): (Example 10) mp.: 270° to 274° C. (dec.) NMR ($D_2O$) δ: 3.13 (2H, m); 4.19 (2H, t); 4.98 (2H, s); 6.72 (1H, m); 7.20 (1H, m); 7.97 (1H, s); 8.77 (1H, s)

Ib-5 (R=3-methyl-5-isoxazolyl): (Example 11) mp.: 266° to 272° C. (dec.) NMR ($D_2O$) δ: 2.42 (3H, s); 3.24 (2H, t); 4.24 (2H, t); 5.10 (2H, s); 7.11 (1H, s); 9.05 (1H, s)

Ib-6 (R=2-pyridyl) (dihydrochloride): (Example 12) mp.: 265° to 281° C. (dec.) NMR ($D_2O$) δ: 3.13 (2H, t); 4.19 (2H, t); 5.00 (2H, s); 7.58 (1H, m); 7.95 to 7.97 (2H, m); 8.63 (1H, d); 8.68 (1H, s)

EXAMPLES 13 to 19

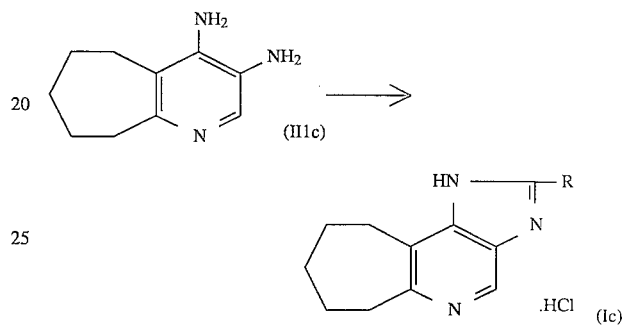

The following compounds are obtained by the use of Compound (IIIc) as a starting compound in the same manner as in Example 1.

Ic-1 (R=phenyl): (Example 13) mp.: 253° to 258° C. (dec.) NMR (DMSO) δ: 1.72 to 1.96 (6H, m); 3.01 (4H, m); 7.31 to 7.59 (5H, m); 8.30 (1H, s)

Ic-2 (R=4-chlorophenyl): (Example 14) mp.: 298° to 320° C. (dec.) NMR (DMSO) δ: 1.68 to 1.92 (6H, m); 3.33 (4H, m); 7.72 (2H, d); 8.44 (2H, d); 9.06 (1H, s)

Ic-3 (R=2-thienyl): (Example 15) mp.: 271° to 274° C. NMR ($D_2O$) δ: 1.72 to 1.96 (6H, m); 3.03 (4H, m); 7.07 (1H, t); 7.52 (1H, d); 7.66 (1H, d); 8.23 (1H, s)

Ic-4 (R=3-thienyl): (Example 16) mp.: 264° to 271° C. NMR ($D_2O$) δ: 1.74 to 1.99 (6H, m); 3.07 (4H, m); 7.37 (1H, m); 7.52 (1H, m); 8.03 (1H, m); 8.40 (1H, s)

Ic-5 (R=2-furyl): (Example 17) mp.: 250° to 261° C. (dec.) NMR ($D_2O$) δ: 1.75 to 1.99 (6H, m); 3.10 (4H, m); 6.74 (1H, m), 7.24 (1H, m); 7.82 (1H, d); 8.52 (1H, s)

Ic-6 (R=3-isoxazolyl): (Example 18) mp.: 191° to 193° C. (dec.) NMR ($D_2O$) δ: 1.78 to 2.02 (6H, m); 3.24 (4H, m); 7.15 (1H, m); 8.86 (1H, s); 8.96 (1H, m)

Ic-7 (R=3-methyl-5-isoxazolyl): (Example 19) mp.: 243° to 260° C. (dec.) NMR ($D_2O$) δ: 1.77 to 2.03 (6H, m); 2.43 (3H, s); 3.23 (4H, m); 7.14 (1H, s); 8.84 (1H, s)

EXAMPLES 20 to 24

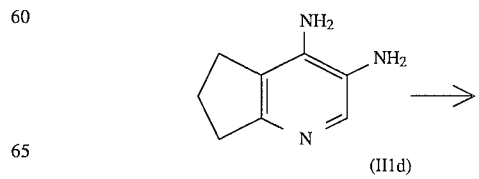

-continued

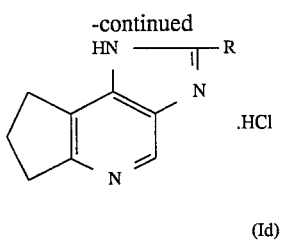

(Id)

The following compounds are obtained by the use of Compound (IIId) as a starting compound in the same manner as in Example 1.

Id-1 (R=3-isoxazolyl): (Example 20) mp.: 252° to 256° C. (dec.) NMR (D$_2$O) δ: 2.46 (2H, m); 3.27 (2H, t); 3.31 (2H, t); 7.09 (1H, m) 8.94 (1H, m); 8.95 (1H, s)

Id-2 (R=3-methyl-5-isoxazolyl): (Example 21) mp.: 290° to 293° C. (dec.) NMR (D$_2$O) δ: 2.42 (3H, s); 2.45 (2H, m); 3.25 (2H, m); 3.30 (2H, m); 7.05 (1H, s); 8.91 (1H, m)

Id-3 (R=2-pyridyl): (Example 22) mp.: 242° to 256° C. (dec.) NMR (D$_2$O) δ: 2.38 (2H, m); 3.17 (4H, t); 7.67 (1H, m); 8.00 to 8.12 (2H, m); 8.67 (1H, m); 8.76 (1H, s)

Id-4 (R=4-methoxyphenyl): (Example 23) mp.: 309° to 316° C. (dec.) NMR (D$_2$O) δ: 2.45 (2H, m); 2.86 to 2.99 (4H, m); 3.69 (3H, s); 6.54 (2H, d); 7.19 (2H, d); 8.30 (1H, s)

Id-5 (R=4-methylphenyl): (Example 24) mp.: 330° C. (dec.) NMR (D$_2$O) δ: 2.18 (3H, s); 2.22 (2H, m); 2.88 (4H, m); 6.92 (2H, d); 7.19 (2H, d); 8.25 (1H, s)

EXAMPLE 25

2-(3-Isoxazolyl)-1,6,7,9-tetrahydroimidazo[4,5-d]pyrano[4,3-b]pyridine (Ib-7)

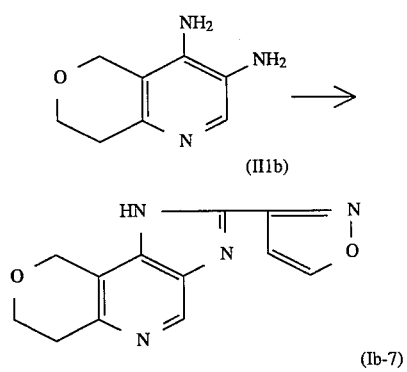

(Ib-7)

To a solution of 5.88 g of 3,4-diamino-7,8-dihydro-5H-pyrano[4,3-b]pyridine (IIIb) (synthesized in Reference Example 1) in 50 ml of dimethylformamide is added a solution of 4.43 g of 3-isoxazolyl chloride in 4.7 ml of methylene chloride with ice cooling, and the resultant mixture is stirred at room temperature for 45 minutes, mixed with 4.7 ml of triethylamine and stirred for 1 hour. The reaction mixture is filtered, and the resultant crystals are mixed with 500 mg of sodium acetate and 79 ml of ethylene glycol and heated at 150° C. (on an oil bath) for 5 hours. The solvent is evaporated in vacuo to dryness, and the resulting residue is chromatographed on a silica gel column, eluting with 10% methanol/chloroform. The product is recrystallized from chloroform-isopropanol to give 5.76 g of Compound (Ib-7) as white crystals melting at 345° to 347° C. (dec.). Yield: 74% Elemental Analysis (%) C$_{12}$H$_{12}$N$_4$O$_2$ Calculated: C, 59.50; H, 4.16; N, 23.12 Found: C, 59.33; H, 4.23; N, 22.91 NMR (d$_6$-DMSO) δ: 2.98 (2H, t); 4.05(2H, t); 5.01 (2H, s); 7.23 (1H, d); 8.83 (1H, s); 9.21 (1H, d)

EXAMPLE 26

2-(5-Isoxazolyl)-1,6,7,9-tetrahydroimidazo[4,5d]pyrano[4,3-b]-pyridine (Ib-8)

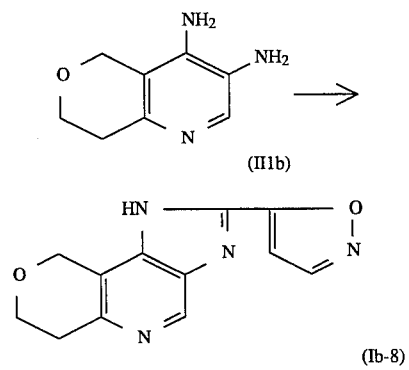

(Ib-8)

To a solution of 264 mg of 5-isoxazolecarboxylic acid in a mixture of 3.5 ml of hexamethylphosphoric triamide and 0.4 ml of acetonitrile is dropwise added 272 mg of thionyl chloride at 0° C. The resultant mixture is stirred at the same temperature for 30 minutes, mixed with 350 mg of Compound (IIIb) and stirred for 4 hours. The reaction mixture is diluted with ice water and neutralized with sodium bicarbonate. The precipitated crystals are dissolved in 14 ml of ethylene glycol, heated at 150° C. for 3.5 hours and the solvent is evaporated in vacuo. The residue is chromatographed on a silica gel column, eluting with methylene chloride-methanol (30:1). The product is recrystallized from methanol-ethyl acetate to give 170 mg of Compound (Ib-8) as colorless crystals melting at 329° to 333° C. (dec.). Yield: 33% Elemental Analysis (%) C$_{12}$H$_{10}$N$_4$O$_2$.1/3H$_2$O Calculated: C, 58.06; H, 4.33; N, 22.57 Found: C, 58.06; H, 4.35; N, 22.42 NMR (D$_6$-DMSO) δ: 2.99 (2H, t); 4.05 (2H, t); 5.01 (2H, s); 7.22 (1H, d); 8.82 (1H, d); 8.84 (1H, s)

EXAMPLE 27

2-Phenyl-1,6,7,9-tetrahydroimidazo[4,5-d]pyrano[4,3-b]pyridine (Ib-9)

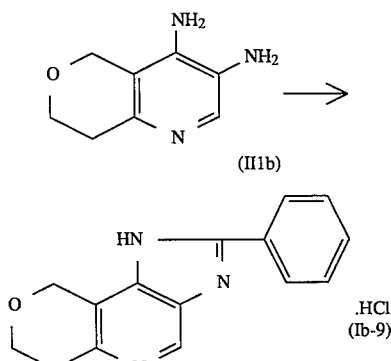

(Ib-9)

To 6 g of polyphosphoric acid are added 400 mg of

Compound (II1b) and 347 mg of benzoic acid, and the mixture is heated on an oil bath at 130° C. for 5 hours. After cooling, the reaction mixture is mixed with ice water, made alkaline with aqueous ammonia and the precipitated crystals are filtered. The filtrate is extracted with 10% methanol/chloroform. The crystals are combined with the extract and chromatographed on a silica gel column, eluting with 5% methanol/chloroform. The product is converted into the hydrochloride in a conventional manner and recrystallized from methanol/isopropanol to give 559 mg of the titled Compound (Ib-9) as white crystals. Yield: 89% mp.: 269° to 286° C. (dec.) NMR (DMSO) δ: 3.17 (2H, t); 3.42 (1H, br.s); 4.90 (2H, t); 5.16 (2H, s); 7.62 to 7.66 (3H, m); 8.35 to 8.44 (2H, m); 9.24 (1H, s) Elemental Analysis (%) $C_{15}H_{13}ON_3 \cdot HCl$ Calculated: C, 62.61; H, 4.90; N, 14.60; Cl, 12.32 Found: C, 62.67; H, 5.01; N, 14.80; Cl, 12.38

EXAMPLE 28

Alternative Synthetic Method of Compound (Ib-7)

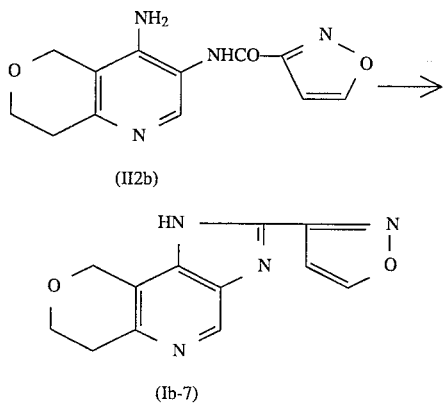

A mixture of 260 mg of isoxazolylaminopyridine (II2b) (synthesized in Reference Example 2) and 4 ml of ethylene glycol is heated at 150° C. for 3 hours. The solvent is evaporated in vacuo, and the residue is dissolved while heated in aqueous ethanol and decolored over active carbon. The precipitated solid is filtered to give 206 mg of Compound (Ib-7) as colorless crystals. Yield: 85%. The crystals were identified as the compound obtained in Example 25 by comparing the melting point and spectra. Further, the following salts of Compound (Ib-7) are synthesized in a conventional manner.

(1) Hydrochloride: mp. 321° to 325° C. (dec.) Elemental Analysis (%) $C_{12}H_{11}N_4O_2Cl \cdot 1/4H_2O$ Calculated: C, 50.89; H, 4.09; N, 19.78; Cl, 12.52 Found: C, 50.90; H, 4.13; N, 19.50; Cl, 12.38

(2) Phosphate: mp. 239° to 241° C. (dec.) Elemental Analysis (%) $C_{12}H_{13}N_4O_6P \cdot H_2O$ Calculated: C, 40.23; H, 4.22; N, 15.63 Found: C, 40,05; H, 4.19; N, 15.39

(3) Methanesulfonate: mp. 219° to 222° C. (dec.) Elemental Analysis (%) $C_{13}H_{14}N_4O_5S \cdot 1/3H_2O$ Calculated: C, 45.35; H, 4.29; N, 16.21; S, 9.31 Found: C, 45.17; H, 4.16; N, 16.19; S, 9.56

(4) Maleate: mp. 331° to 336° C. (dec.) Elemental Analysis (%) $C_{16}H_{14}N_4O_6$ Calculated: C, 53.63; H, 3.93; N, 15.63 Found: C, 53.73; H, 3.93; N, 15.62

EXAMPLE 29

2-(3-Isoxazolyl)-7,7-dimethyl-1H-imidazo[4,5-d]-cyclopenta[b]pyridine (Ic-1)

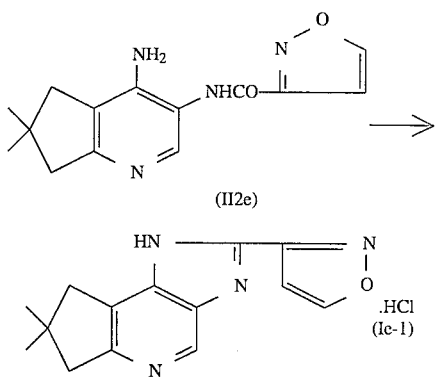

A mixture of 2.05 g of 4-amino-3-(3-isoxazolylamino)-6,6-dimethylcyclopenta[b]pyridine (II2e) and 21 ml of ethylene glycol is heated at 150° C. for 3.5 hours, and the solvent is evaporated in vacuo. The residue is chromatographed on a silica gel column, eluting with methylene chloride-methanol (30/1). The product is dissolved in methanol and mixed with methanolic hydrochloric acid to give 1.90 g of Compound (Ie-1). Yield: 82% mp.: 270° to 272° C. Elemental Analysis (%) $C_{14}H_{15}N_4OCl$ Calculated: C, 57.83; H, 5.19; N; 19.26; Cl, 12.19 Found: C, 57.53; H, 5.31; N, 19.09; Cl, 12.31 NMR (d$_6$-DMSO) δ: 1.26 (6H, s); 3.08 (2H, s); 3.12 (2H, s); 7.40 (1H, d); 9.34 (1H, d)

EXAMPLE 30

2-(3-Isoxazolyl)-8-ethoxycarbonyl-6,7,8,9-tetrahydro-1H-imidazo[4,5-c]naphthylidine (Ig-1)

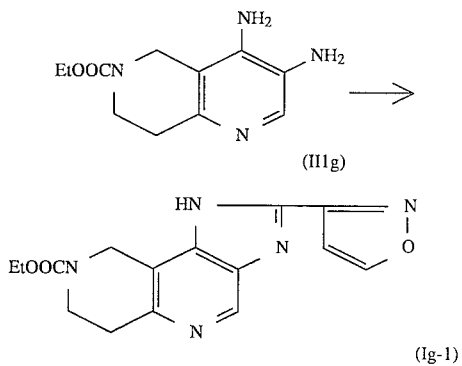

To a solution of 274 mg of 3-isoxazolecarboxylic acid in a mixture of 3.5 ml of hexamethyl phosphotriamide and 0.5 ml of acetonitrile is dropwise added 288 mg of thionyl chloride at 0° C., and the resultant mixture is stirred at the same temperature for 30 minutes. To the mixture is added 520 mg of 3,4-diamino-6-ethoxycarbonyl-5,6,7,8-tetrahydro [1,6]naphthylidine (III g) (synthesized in Reference Example 3), and the mixture is stirred for 4 hours. The reaction mixture is diluted with ice water, neutralized with sodium bicarbonate and extracted with methylene chloride, the extract is dissolved in 15 ml of ethylene glycol and heated at 150° C. for 4 hours. The solvent is evaporated in vacuo, and the residue is chromatographed on a column of silica gel, eluting with methylene chloride-methanol (50:1). The product is recrystallized from methanol/ethyl acetate to give 410 mg of Compound (Ig-1). Yield: 60% mp.: 271° to 273° C. (dec.) Elemental Analysis (%) $C_{15}H_{15}N_5O_3$ Calculated: C, 57.50; H, 4.82; N, 22.35 Found: C, 57.47; H, 5.02; N, 22.25 NMR ($d_6$-DMSO) δ: 1.24 (3H, t); 2.99 (2H, t); 3.79 (2H, t); 4.13 (2H, q); 4.90 (2H, s); 7.28 (1H, d); 8.82 (1H, s); 9.22 (1H, d)

EXAMPLE 31

2-(3-Isoxazolyl)-1,6,7,9-tetrahydroimidazo[4,5-d]-thiopyrano[4,3-b]pyridine (If-1)

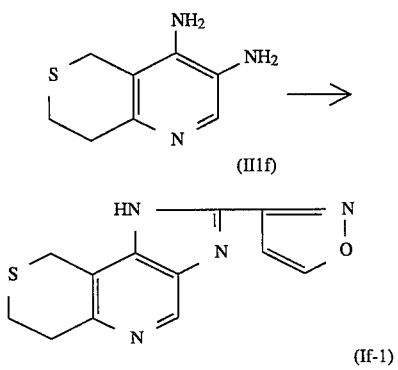

Compound (IIIf) is used as a starting compound in the same manner as in Example 26 to give Compound (If-1). mp.: 253° to 255° C. (dec.) Elemental Analysis (%) $C_{12}H_{10}N_4OS.1/6H_2O$ Calculated figure: C, 55.16; H, 3.99; N, 21.44; S, 12.27 Measured figure: C, 55.17; H, 4.21; N, 21.23; S, 12.05 NMR ($D_6$-DMSO) δ: 3.04 (2H, t); 3.20 (2H, t); 4.13 (2H, s); 7.24 (1H, d); 8.81 (1H, s); 9.21 (1H, d); 13.76 (1H, br.s, NH)

EXAMPLE 32

2-(3-Isoxazolyl)-6,7,8,9-tetrahydro-1H-imidazo[4,5-c]quinoline (Ia-7)

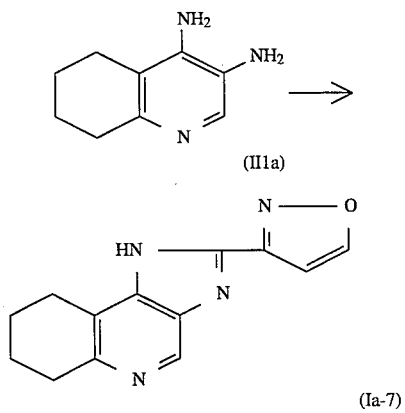

Compound (IIIa) is used as a starting compound in the same manner as in Example 26 to give Compound (Ia-7). mp.: 222° to 225° C. Elemental Analysis (%) $C_{13}H_{12}N_4O$ Calculated: C, 63.41; H, 5.18; N, 22.75 Found: C, 63.42; H, 5.18; N, 22.48 NMR ($d_6$-DMSO) δ: 1.86 (4H, m); 2.92 (2H, m); 2.99 (2H, m); 7.22 (1H, d); 8.75 (1H, s); 9.19 (1H, d)

EXAMPLE 33

2-(3-Isoxazolyl)-1H-imidazo[4,5-d]cyclopenta[b]pyridine (Id-1)

Compound (IIId) is used as a starting compound in the same manner as in Example 26 to give Compound (Id-1). mp.: 250° to 255° C. Elemental Analysis (%) $C_{12}H_{10}N_4O.1/3H_2O$ Calculated: C, 62.06; H, 4.63; N, 24.12 Found: C, 61.97; H, 4.61; N, 23.97 NMR ($d_6$-DMSO) δ: 2.18 (2H, m); 3.02 (2H, t); 3.14 (2H, t); 7.25 (1H, d); 8.77 (1H, s); 9.22 (1H, d)

EXAMPLE 34

2-(3-Isoxazolyl)-6,7,8,9-tetrahydro-1H-imidazo[4,5-c]-naphthylidine (Ig-2)

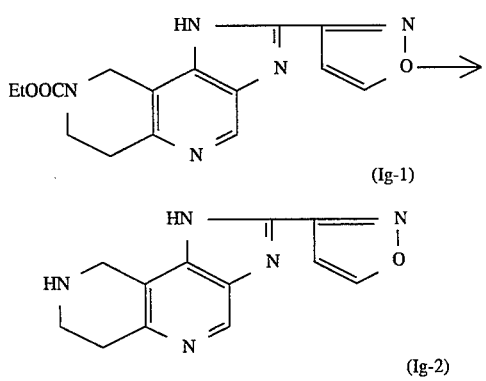

A mixture of 490 mg of Compound (Ig-1) obtained in Example 30 and 25% hydrobromic acid/acetic acid (25 ml) was stirred at 70° C. for 5 hours. After the solvent is evaporated in vacuo, the residue is neutralized with aqueous sodium bicarbonate and concentrated in vacuo to dryness. The residue is shaken with chloroform/methanol and the resultant solution is concentrated. The residue is chromatographed on an alumina column, eluting with methylene chloride-methanol (10:1). The product is recrystallized from methanol-ethyl acetate to give 335 mg of Compound (Ig-2) as crystals melting at 278° to 281° C. (dec.). Yield: 89% Elemental Analysis (%) $C_{12}H_{11}N_5O$ Calculated: C, 59.74; H, 4.59; N, 29.02 Found: C, 59.54; H, 4.71; N, 29.31 NMR ($d_6$-DMSO) δ: 2.87 (2H, t); 3.10 (2H, t); 4.15 (2H, s); 7.21 (1H, d); 8.76 (1H, s); 9.18 (1H, d)

EXAMPLE 35

2-(3-Isoxazolyl)-8-acetyl-1-6,7,8,9-tetrahydro-1H-imidazo[4,5-c]naphthylidine (Ig-3)

To a mixture of 95 mg of Compound (Ig-2) obtained in the foregoing Example and 5 ml of methylene chloride are added 160 mg of triethylamine and 160 mg of acetic anhydride and the resultant mixture is stirred at room temperature for 1 hour. After the solvent is evaporated in vacuo, the residue is recrystallized from ethyl acetatemethylene chloride to give 68 mg of the acetylate (Ig-3). Yield: 61% mp.: 236° to 240° C. Elemental Analysis (%) $C_{14}H_{13}N_5O_2.1/4H_2O$ Calculated: C, 58.43; H, 4.73; N, 24.33 Found: C, 58.52; H, 4.62; N, 24.20 NMR ($d_6$-DMSO) δ: 2.52 (3H, s); 3.31 (2H, t); 3.96 (2H, t); 5.35 (2H, s); 7.13 (1H, d); 8.57 (1H, d); 8.99 (1H, s)

EXAMPLE 36

2-(3-isoxazolyl)-8-methyl-6,7,8,9-tetrahydro-1H-imidazo[4,5-c]naphthylidine (Ig-4)

To a solution of 680 mg of Compound (Ig-1) obtained in Example 30 is added 330 mg of lithium aluminum hydride, and the resultant mixture is refluxed for 6 hours. After the reaction mixture is chilled with ice, the mixture is mixed with 0.5 ml of 2N aqueous sodium hydroxide and stirred at room temperature for 30 minutes. The precipitate is filtered and the filtrate is concentrated. The residue is chromatographed on an alumina column, eluting with methylene chloride-methanol (50/1). The product is treated with hydrochloric acid to give 340 mg of Compound (Ig-4) hydrochloride. Yield: 53% mp.: 243° to 247° C. (dec.) Elemental Analysis (%) $C_{13}H_{15}N_5OCl \cdot H_2O$ Calculated: C, 45.09; H, 4.94; N, 20.22; Cl, 24.48 Found: C, 45.07; H, 5.07; N, 19.95; Cl, 20.75

Reference Example 1

Preparation of 3,4-diamino-5,6,7,8-tetrahydroquinoline (IIIa)

3-Amino-5,6,7,8-tetrahydroquinoline 1

A suspension of 15.8 g of 3-nitro-5,6,7,8-tetrahydroquinoline [synthesized according to the method as described in Bull. Chem. Soc. Jpn. Vol. 63 (1990), 2820] and 1.6 g of 5% palladium carbon in 300 ml of methanol is hydrogenerated at ordinary temperature under atmospheric pressure. The catalyst is filtered off, and the filtrate is concentrated in vacuo to remove the solvent. The resultant crude product is recrystallized from methylene chloride-isopropyl ether to give 12.76 g of the titled compound 1. Yield: 97% mp.: 97° to 98° C.

(2) 3-Trichloroacetylamino-5,6,7,8-tetrahydroquinoline 2

To 130 ml of methylene chloride are added 12.69 g of Compound 1 obtained in the above step (1) and 2.4 ml of triethylamine, and a solution of 10.5 ml of trichloroacetyl chloride in 30 ml of methylene chloride is dropwise added with ice cooling and under stirring over a period of 7 minutes. The reaction mixture is stirred at room temperature for 20 minutes, mixed with saturated saline, made weakly alkaline with aqueous ammonia and the organic layer is separated. The aqueous layer is shaken with methylene chloride. The organic layers are combined, washed with saturated saline, dried over anhydrous magnesium sulfate and concentrated to remove the solvent. The residue is chromatographed on a silica gel column, eluting with 10% methanol/methylene chloride. The product is recrystallized from ethyl acetate to give 24.21 g of the titled compound 2. Yield: 96% mp.: 157° to 159° C.

(3) 3-Trichloroacetylamino-5,6,7,8-tetrahydroquinoline-1-oxide 3

To a solution of 24.03 g of Compound 2 obtained in the above step (2) in 40 ml of methylene chloride is added 21.2 g of 80% m-chloroperbenzoic acid at room temperature, and the resultant mixture is stirred for 45 minutes. The reaction mixture is mixed with isopropyl ether and the crystals are filtered to give 25.06 g of the titled compound 3 as crystals. Yield: 99% mp.: 244° to 246° C. (dec.)

(4) 3-Amino-4-nitro-5,6,7,8-tetrahydroquinoline-1-oxide 4

A mixture of 1.00 g of Compound 3 obtained in the above step (3) and 5.0 ml of fuming nitric acid (d=1.52) is stirred at 55° C. on an oil bath for 5 hours. The fuming nitric acid is evaporated in vacuo, and the residue is neutralized with aqueous ammonia and heated at 60° C. on an oil bath for 2 hours. The reaction mixture containing crystals is mixed with 10 ml of 50% isopropyl ether/isopropanol, and the resulting precipitate is filtered. The filtrate is concentrated in vacuo and extracted with 10% methanol/chloroform. The crystals are combined with the residue and chromatographed on an alumina column, eluting with 2% methanol/chloroform. The product is recrystallized from methylene chloride-isopropanol to give 525 mg of the titled compound 4 as brownish red crystals. Yield: 78% mp.: 199° to 201° C.

(5) 3,4-Diamino-5,6,7,8-8-tetrahydroquinoline (IIIa)

A mixture of 5.00 g of Compound 4 obtained in the above step (4) and 12.9 g of Raney nickel in methanol is hydrogenated at ordinary temperature under atmospheric pressure. The catalyst is filtered off, and the filtrate is concentrated in vacuo to remove the solvent. The residue is chromatographed on an alumina column, eluting with 5% methanol/chloroform. The product is recrystallized from methylene chloride-ethyl acetate to give 3.37 g of the titled compound (IIIa) as crystals. Yield: 86% mp.: 169° to 170° C. (dec.) Elemental Analysis (%) $C_9H_{13}N_3$ Calculated: C, 66.22; H, 8.03; N, 25.75 Found: C, 65.93; H, 8.00; N, 25.50 NMR ($d_6$-DMSO) δ: 1.68 (4H, m); 2.38 (2H, t); 2.54 (2H, t); 4.26 (2H, s, NH); 4.97 (2H, s, NH); 7.47 (1H, s)

The reaction is effected in the same manner as above to give Compounds (IIIb) (IIIc) and (IIId).

(IIIb): mp. 196° to 200° C. (dec.) Elemental Analysis $C_8H_{11}N_3O \cdot H_2O$ Calculated: C, 52.45; H, 7.15; N, 22.94 Found: C, 52.18; H, 7.08; N, 22.71 NMR (CDCl$_3$) δ: 2.88 (2H, t); 3.05 (2H, br.s); 3.84 (2H, s); 4.00 (2H, t); 4.63 (2H, s); 7.87 (1H, s)

(IIIc): mp. 167° to 168° C. Elemental Analysis (%) $C_{10}H_{15}N_3$ Calculated: C, 67.76; H, 8.53; N, 23.71 Found: C, 67.76; H, 8.48; N, 23.47 NMR ($d_6$-DMSO) δ: 1.48 to 1.74 (6H, m); 2.58 (2H, m); 2.70 (2H, m); 4.26 (2H, s, NH); 5.02 (2H, s, NH); 7.36 (1H, s)

(IIId): mp. 190° to 193° C. Elemental Analysis (%) $C_8H_{11}N_3$ Calculated: C, 64.40; H, 7.43; N, 28.17 Found: C, 64.43; H, 7.37; N, 28.02 NMR ($d_6$-DMSO) δ: 1.94 (2H, m); 2.61 (2H, t); 2.63 (2H, t); 4.26 (2H, s, NH); 5.08 (2H, s, NH); 7.43 (1H, s)

Reference Example 2

Preparation of 4-amino-3-(3-isoxazolyl)amino-7,8-dihydro-5H-pyrano[4,3-b]pyridine (II2b)

(1) 3-(3-Isoxazolyl)amino-7,8-dihydro-5H-pyrano[4,3-b]pyridine-1-oxide 5

To a solution of 2.00 g of 3-nitro-7,8-dihydro-5H-pyrano[4,3-b]pyridine [prepared according to the method as described in Bull. Chem. Soc. Jpn. Vol. 63 (1990), 2820] in 40 ml of methylene chloride is added 2.63 g of m-chloroperbenzoic acid, and the resultant mixture is stirred overnight. The reaction mixture is washed with aqueous potassium carbonate, dried over anhydrous magnesium sulfate and the solvent is evaporated. The crude product is recrystallized from ethanol-chloroform to give 1.82 g of 3-nitro-7,8-dihydro-5H-pyrano[4,3-b]pyridine-1-oxide as colorless crystals. Yield: 84%. To a solution of 1.47 g of the product in 75 ml of methanol-dimethylformamide (1:1) is added 100 mg of 10% palladium carbon, and the resultant mixture is hydrogenated at ordinary temperature under atmospheric pressure. After the reduction is completed in about 3 hours, the catalyst is filtered off. The resultant crude crystals are washed with ethanol to give 1.08 g of 3-amino-1-oxide as colorless crystals. Yield: 86%. To a solution of 690 mg of 3-isoxazolylcarbonyl chloride in 20 ml of dimethylformamide is added 414 mg of pyridine under ice cooling, and then 830 mg of 3-amino-1-oxide as crystals is added. The resultant mixture is stirred under ice cooling for 30 minutes and at room temperature for 1 hour, chilled again with ice, and mixed with 4 ml of water. The suspension is neutralized with sodium bicarbonate. The precipitated solid is filtered, washed with water and ethanol in this order and dried to give 1.13 g of the titled compound as colorless crystals. Yield: 86%. ml.: 260° to 265° C. (dec.)

(2) 3-(3-Isoxazolyl)amino-4-nitro-7,8-dihydro-5H-pyrano[4,3-b]pyridine-1-oxide 6

A solution of 653 mg of Compound 5 obtained in the above step (1) as crystals in 3.2 ml of fuming nitric acid is stirred at 55° C. for 3 hours. The reaction mixture is chilled, poured onto ice water and shaken with chloroform. The extract is washed with water, aqueous disodium hydrogen phosphate and saturated saline in this order, dried over anhydrous magnesium sulfate and concentrated to remove the solvent. The resultant residue is washed with methanol to give 551 mg of the titled compound as light yellow crystals. Yield: 70% mp.: 174° to 176° C. (dec.)

(3) 3-(3-Isoxazolyl)amino-4-nitro-7,8-dihydro-5H-pyrano[4,3-b]pyridine 7

To a solution of 473 mg of Compound 6 obtained in the above step (2) in 30 ml of methylene chloride is added a solution of 935 mg of phosphorus tribromide in 1 ml of methylene chloride under ice cooling. The reaction mixture is stirred for 2 hours, mixed with ice water and neutralized with aqueous potassium carbonate under ice cooling. The organic layer is separated, and the aqueous layer is extracted with methylene chloride. The organic layers are combined, washed with saturated saline, dried over anhydrous magnesium sulfate and the solvent is evaporated. The residue is recrystallized from methylene chloride-isopropanol to give 407 mg of the titled compound 7 as yellow crystals. Yield: 93% mp.: 143° to 145° C.

(4) Preparation of Compound (II2b)

To a solution of 435 mg of Compound 7 obtained in (3) above in 95% aqueous methanol is added 10% palladium carbon (40 mg) as catalyst, and the resultant mixture is hydrogenated at ordinary temperature under atmospheric pressure. The reaction mixture is filtered, and the hardly soluble solid is washed out with dimethylformamide. The filtrate is concentrated in vacuo, and the residue is recrystallized from methanol-methylene chloride to give 280 mg of the titled compound (II2b) as light brown crystals. Yield: 72% mp.: 209° to 211° C. Elemental Analysis (%) $C_{12}H_{12}N_4O_3$ Calculated: C, 55.38; H, 4.65; N, 21.53 Found: C, 55.08; H, 4.54; N, 21.24 NMR ($d_6$-DMSO) δ: 2.73 (2H, t); 3.90 (2H, t); 4.51 (2H, s); 5.93 (2H, s, NH); 7.06 (1H, d); 7.93 (1H, s); 9.15 (1H, d); 10.07 (1H, s, NH)

3-Nitro-6,6-dimethylcyclopenta[b]pyridine is used in the same manner as above to give 4-amino-3-(3-isoxazolylamino)-6,6-dimethylcyclopenta[b]pyridine (II2e). mp.: 171° to 174° C. (dec.) Elemental Analysis (%) $C_{14}H_{16}N_4O_2$ Calculated: C, 61.75; H, 5.92; N, 20.57 Found: C, 61.41; H, 6.05; N, 20.13 NMR ($d_6$-DMSO) δ: 1.14 (6H, s); 2.52 (2H, s); 2.61 (2H, s); 5.64 (2H, br.s); 6.99 (1H, d); 7.80 (1H, s); 9.12 (1H, d)

Reference Example 3

Preparation of 3,4-diamino-6-ethoxycarbonyl-5,6,7,8-tetrahydro[1,6]naphthylidine (III1g).

(1) 4-Azido-6-ethoxycarbonyl-5,6,7,8-tetrahydro[1,6]-naphthylidine-6-carboxylic acid 8

A mixture of 3 g of ethyl 6-ethoxycarbonyl-4-hydroxy-5,6,7,8-tetrahydro[1,6]naphthylidine-3-carboxylate and 21 ml of phosphorus oxychloride is refluxed under heating for 90 minutes. The reaction mixture is concentrated in vacuo to dryness, and the residue is mixed with ice water and shaken with methylene chloride. The extract is chromatographed on a silica gel column to give oily 4-chloro compound. This compound is dissolved in 70 ml of dimethylformamide, mixed with 1.72 g of sodium amide and stirred at 70° C. for 3 hours. After the solvent is evaporated in vacuo, the residue is mixed with water and extracted with chloroform. The extract is chromatographed on a silica gel column to give crystalline 4-azido compound. This compound is dissolved in 30 ml of methanol, mixed with 4N aqueous potassium hydroxide, stirred at room temperature for 1 hour and the methanol is evaporated in vacuo. The residue is made weakly acidic with dilute hydrochloric acid, and the precipitated crystals are filtered and washed to give 1.89 g of 4-azido-3-carboxylic acid 8 as crystals. Yield: 64% mp.: 171° to 175° C. (dec.)

(2). 4-Azido-6-ethoxycarbonyl-3-t-butoxycarbonylamino-5,6,7,8-tetrahydro[1,6]naphthylidine 9

To a solution of 3.4 g of Compound 8 obtained in the above step (1) in 100 ml of tetrahydrofuran is added 1.42 g of triethylamine, and 1.52 g of ethyl chloroformate is dropwise added at −10° to −5° C. After stirring is continued at the same temperature for 1 hour, a solution of 3.81 g of sodium azide in 15 ml of water is dropwise added to the mixture, which is stirred at 0° C. for 1 hour. The reaction mixture is concentrated in vacuo, and the residue is mixed with water and shaken with methylene chloride. The extract is dissolved in a mixture of 80 ml of dichloroethane and 40 ml of t-butanol, and the resultant solution is refluxed for 1 hour. The solvent is evaporated, and the residue is chromatographed on a silica gel column to give 3.38 g of 3-t-butoxycarbonylamino compound 9 as crystals. Yield: 79% mp.: 144° to 145° C.

(3) Preparation of Compound (III1g)

To a solution of 3.30 g of Compound 9 obtained in the above step (2) in 100 ml of tetrahydrofuran/ethanol (1:1) is dropwise added a solution of 3.15 g of stannous chloride (II) dihydrate in a mixture of 40 ml of 5N aqueous sodium hydroxide and 50 ml of water at −10° C. over a period of 30 minutes, and the resultant mixture is stirred at 0° C. for 20 minutes. The solvent is evaporated in vacuo, and the residue is mixed with water and shaken with ethyl acetate. The extract is dissolved in 130 ml of methylene chloride, mixed with 26 ml of trifluoroacetic acid, and stirred at room temperature for 1 hour. The reaction is concentrated in vacuo, and the residue is mixed with saturated saline and neutralized with 5N aqueous sodium hydroxide. The precipitated crystals are filtered, dissolved in methanol, and the resultant solution is concentrated to give 1.98 g of the titled compound (III1g) as crystals. Yield: 90% mp.: 171° to 174° C. (dec.) Elemental Analysis (%) $C_{11}H_{16}N_4O_2$ Calculated: C, 55.91; H, 6.82; N, 23.71 Found: C, 55.68; H, 6.59; N, 23.79 NMR (CDCl$_3$) δ: 1.31 (3H, t); 2.87 (2H, t); 3.05 (2H, s, NH); 3.75 (2H, t); 3.99 (2H, s, NH); 4.21 (2H, q); 4.42 (2H, s); 7.86 (1H, s)

Ethyl 4-hydroxy-7,8-dihydro-5H-pyrano[4,3-b]pyridine-3-carboxylate and 4-hydroxy-7,8-dihydro-5H-thiopyrano[4,3-b]pyridine-3-carboxylate are reacted in the same manner as in the above steps (1) to (3) to give Compounds (III1b) and (III1f), respectively.

(III1b): The same physico-chemical data were obtained as in the compound (III1b) prepared in Reference Example 1.

(III1f): mp.: 66° to 67° C. NMR (CDCl$_3$) δ: 2.90 (2H, t); 3.06 (2H, s, NH); 3.13 (2H, t); 3.57 (2H, s); 4.03 (2H, s, NH); 7.85 (1H, s)

Reference Example 4

Alternative Synthetic Method of (III1b)

To a solution of 1.50 g of 3-amino-7,8-dihydro-5H-pyrano[4,3-b]pyridine in 45 ml of methylene chloride is added 1.55 ml of trifluoroacetic anhydride with ice cooling and under stirring, and the resultant mixture is stirred at the same temperature for 15 minutes. The reaction mixture is mixed with ice water, made weakly alkaline with aqueous ammonia and extracted with methylene chloride. The extract is washed with saturated saline and the solvent is evaporated. The resultant crude crystals are recrystallized from acetone-isopropyl ether to give 2.14 g of 3-trifluoroacetylamino-7,8-dihydro-5H-pyrano[4,3-b]pyridine as crystals. Yield: 87%. The product (1.55 g) is dissolved in 30 ml of methylene chloride, and 1.63 g of 80% m-chloroperbenzoic acid is added to the solution, which is stirred at room temperature for 2.5 hours. The reaction mixture is mixed with 50 ml of ether, and the precipitated crystals are filtered to give 1.58 g of 3-trifluoroacetylamino-7,8-dihydro-5H-pyrano[4,3-b]pyridine 1-oxide as crystals. Yield: 96%. The product (1.568 g) is mixed with 9.4 ml of fuming nitric acid (d=1.52) and stirred at 55° C. for 6 hours. The reaction mixture is concentrated in vacuo, made alkaline with aqueous ammonia, allowed to stand at room temperature overnight and shaken with 10% methanol/chloroform. The resultant crude crystals are recrystallized from acetone to give 0.85 g of 3-amino-4-nitro-7,8-dihydro-5H-pyrano[4,3-b]pyridine-1-oxide (II1b) as brown crystals. Yield: 67%. Melting point and spectra data confirmed that the product is the same as the compound (II1b) obtained in Reference Example 1.

Reference Example 5

Preparation of 3-amino-4-chloro-5,6,7,8-tetrahydroquinoline (III1a).

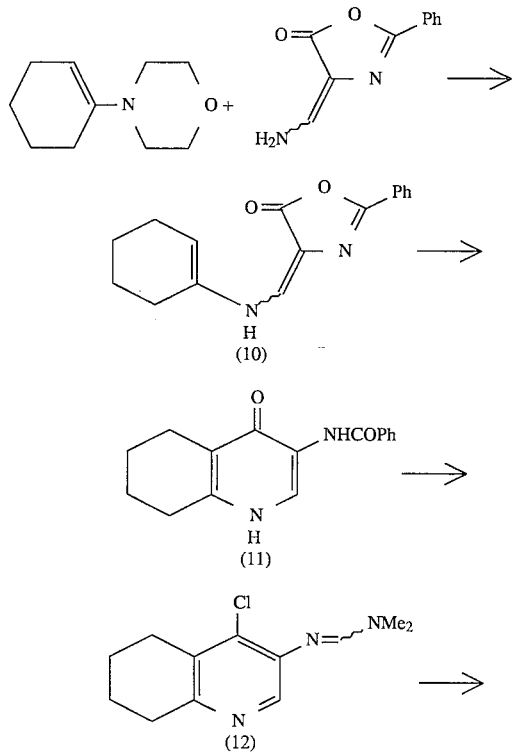

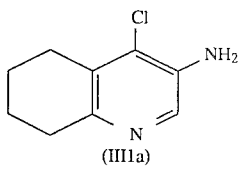

(1) 4-(Cyclohexene-1-ylaminomethylene)-2-phenyl-5(4H)-oxazolone(10)

To 58.5 g of acetic anhydride are added 36.8 g of 1-morpholino-1-cyclohexene and 36 g of 4-aminomethylene-2-phenyl-5(4H)-oxazolone, and the resultant mixture is heated at about 65° C. (bath temperature) for 1.5 hours. The reaction mixture is allowed to cool to room temperature, mixed with 90 ml of isopropyl ether and chilled with ice. The precipitated crystals are filtered to give 39.8 g of Compound (10) as yellow crystals melting at 155° to 157° C. (dec.). Yield: 78%. The crystals can be used for the subsequent reaction without purification, but a small portion is recrystallized from isopropanol/isopropyl ether to give yellow crystals (10) melting at 156° to 158° C. (dec.). Elemental Analysis (%) $C_{16}H_{16}N_2O_2$ Calculated: C, 71.62; H, 6.01; N, 10.44 Found: C, 71.34; H, 6.05; N, 10.30 NMR (CDCl$_3$) δ: 1.71 (4H, m), 2.18 (4H, m), 5.45 (1H, m), 7.26 to 7.49 (3H, m), 7.67 (1H, d, J=14.0 Hz), 7.92 to 8.03 (2H, m), 9.05 (1H, d, J=14.0 Hz, NH)

(2) 3-Benzoylamino-5,6,7,8-tetrahydroquinoline-4(1H)-one(11)

A mixture of 36.8 g of Compound (10) and 55 ml of N-methyl-2-pyrrolidone is stirred with heating at 205° C. (bath temperature) for 30 minutes. After allowing to cool, the reaction mixture is mixed with acetone and chilled with ice. The precipitated crystals are filtered to give 33.6 g of Compound (11). Yield: 91%. This product can be used for the subsequent reaction without purification, but a small portion is recrystallized from chloroform/methanol to give colorless crystals melting at 408° to 410° C. Elemental Analysis (%) $C_{16}H_{16}N_2O_2$ Calculated: C, 71.62; H, 6.01; N, 10.44 Found: C, 71.58; H, 6.01; N, 10.49 NMR (d$_6$-DMSO) δ: 1.45 (2H, m), 1.60 to 1.65 (2H, m), 1.79 (2H, m), 2.73 to 2.78 (4H, m), 7.52 to 7.63 (3H, m), 7.87 to 7.92 (2H, m), 8.55 (1H, d, J=6.0 Hz), 9.39 (1H, s, NH), 11.44 (1H, br d, NH)

(3) 4-Chloro-3-(N,N-dimethylaminomethyleneamino)-5,6,7,8-tetrahydroquinoline(12)

To a suspension of 5.36 g of Compound (11) in 26 ml of dimethylformamide is dropwise added a solution of 2.8 ml of phosphorus oxychloride in 8 ml of dimethylformamide at temperature from −10° to −5° C., and the temperature is gradually raised up to room temperature. The reaction mixture is stirred overnight, chilled with ice, poured onto ice water and extracted with methylene chloride to remove the acidic and neutral by-products. The aqueous layer is made alkaline with conc. aqueous ammonia under ice cooling and shaken with ethyl acetate. The extract is washed with saturated saline, dried and concentrated in vacuo. The residue is chromatographed on an alumina column, eluting with methylene chloride/acetonitrile (40:1) to give 3.73 g of Compound (12) as colorless crystals melting at 62° to 64° C. Yield: 79%. Elemental Analysis (%) $C_{12}H_{16}N_3Cl$ Calculated: C, 60.62; H, 6.79; N, 17.68; Cl, 14.92 Found: C, 60.70; H, 6.83; N, 17.75; Cl, 14.77 NMR (CDCl$_3$) δ: 1.79 to 1.87 (4H, m), 2.77 to 2.88 (4H, m), 3.06 (6H, s), 7.45 (1H, s), 7.90 (1H, s)

(4) 3-Amino-4-chloro-5,6,7,8-tetrahydroquinoline(III1a)

A solution of 3.60 g of Compound (12) in 25 ml of 3N sulfuric acid is stirred at 100° C. (bath temperature) for 1.5 hours. The reaction mixture is made alkaline with aqueous ammonia, mixed with saline and extracted with methylene chloride. The extract is dried and concentrated to give 2.61 g of Compound (III1a) as colorless crystals melting at 114° to 117° C. (dec.). Yield: 94%. The crystals can be used for the subsequent reaction without purification, but a small portion is recrystallized from methylene chloride/isopropyl ether to give colorless crystals melting at 115° to 117° C. (dec.). Elemental Analysis (%) $C_9H_{11}N_2Cl$ Calculated: C, 59.18; H, 6.07; N, 15.34; Cl, 19.41 Found: C, 59.05; H, 6.03; N, 15.30; Cl, 19.32 NMR (CDCl$_3$) δ: 1.78 to 1.87 (4H, m), 2.72 to 2.85 (4H, m), 3.91 (2H, br s, NH 2), 7.96 (1H, s)

Reference Examples 6 to 8

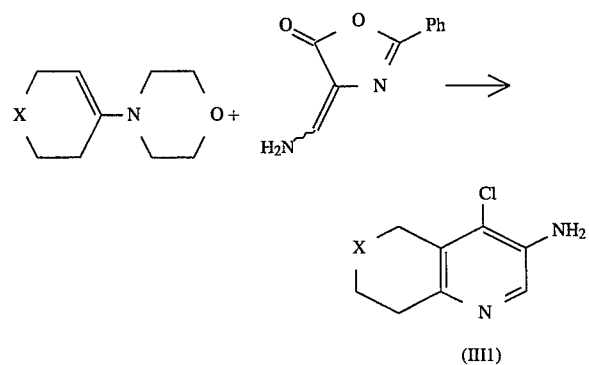

Using the corresponding enamines, the reaction is effected in the same manner as in Reference Example 5 to give the following compounds.

III1b (X=O): (Reference Example 6) mp.: 125° to 127° C. Elemental Analysis (%) $C_8H_9N_2OCl$ Calculated: C, 52.04; H, 4.91; N, 15.18; Cl, 19.20 Found: C, 52.08; H, 4.88; N, 15.12; Cl, 19.44 NMR (CDCl$_3$) δ: 2.91 (2H, t, J=5.8 Hz), 4.00 (2H, t, J=5.8 Hz), 4.00 (2H, br s, NH2), 4.75 (2H, AB-q), 8.05 (1H, s)

III1c (X=—CH$_2$CH$_2$—): (Reference Example 7) mp.: 144° to 146° C. Elemental Analysis (%) $C_{10}H_{13}N_2Cl$ Calculated: C, 61.06; H, 6.66; N, 14.24; Cl, 18.02 Found: C, 61.06; H, 6.63; N, 14.25; Cl, 18.14 NMR (CDCl$_3$) δ: 1.60 to 1.72 (4H, m), 1.79 to 1.88 (2H, m), 2.94 to 2.99 (4H, m), 3.94 (2H, br s, NH2), 7.84 (1H, s)

III1f (X=S): (Reference Example 8) mp.: 129° to 132° C. Elemental Analysis (%) $C_8H_9N_2SCl$ Calculated: C, 47.87; H, 4.51; N, 13.95; S, 15.97; Cl, 17.66 Found: C, 47.79; H, 4.52; N, 13.93; S, 16.10; Cl, 17.52 NMR (CDCl$_3$) δ: 2.92 (2H, t, J=6.2 Hz), 3.15 (2H, t, J=6.2 Hz), 3.84 (2H, s), 4.00 (2H, br s, NH2), 8.02 (1H, s)

Reference Example 9

Preparation of 4-chloro-3-(isoxazole-3-carbonylamino)-5,6,7,8-tetrahydroquinoline (III2a-1)

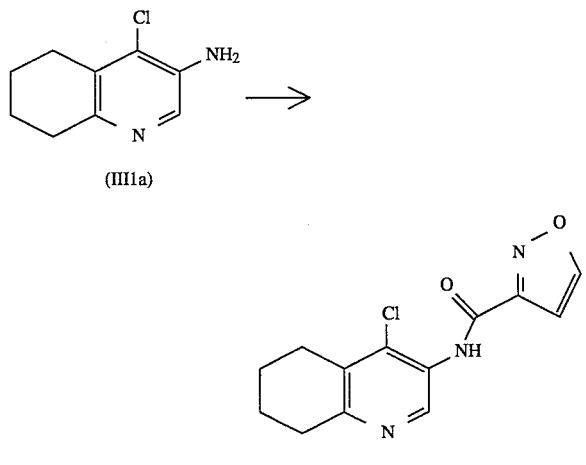

To a solution of 4.20 g of 3-amino-4-chloro-5,6,7,8-tetrahydroquinoline (III1a) and 1.96 g of pyridine in 80 ml of methylene chloride is added a solution of 3.24 g of isoxazole-3-carbonyl chloride in 4 ml of methylene chloride, and the resultant mixture is stirred at room temperature for 2 hours. The reaction mixture is mixed with ice water, adjusted to pH 10 with conc. aqueous ammonia to pH 10, and stirred at room temperature for 10 minutes. The organic layer is separated, and the aqueous layer is extracted with methylene chloride. The combined extracts are washed with water, dried and the solvent is evaporated to give 5.9 g of Compound (III2a-1) as crystals melting at 150° to 153° C. (dec.). Yield is 92%. The crystals can be used for the subsequent reaction without purification, but a small portion is recrystallized from isopropyl ether/methylene chloride to give colorless crystals melting at 151° to 153° C. (dec.). Elemental Analysis (%) $C_{13}H_{12}N_3O_2Cl$ Calculated: C, 56.22; H, 4.35; N, 15.13; Cl, 12.76 Found: C, 56.12; H, 4.41; N, 15.26; Cl, 12.91 NMR (CDCl$_3$) δ: 1.85 to 1.91 (4H, m), 2.78 to 2.85 (2H, m), 2.92 to 2.98 (2H, m), 6.94 (1H, d, J=1.6 Hz), 8.56 (1H, d, J=1.6 Hz), 8.96 (1H, br s, NH), 9.38 (1H, s)

Reference Examples 10 to 14

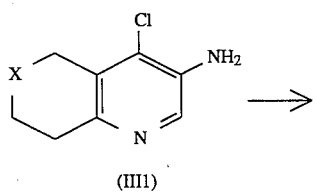

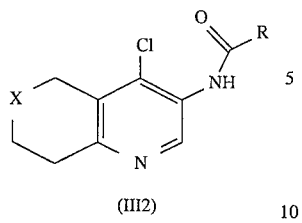

(III2)

Using the corresponding pyridine derivatives (III1a), (III1b), (III1c) and (III1f), the reaction is effected as in Reference Example 9 to give the following compounds.

III2a-2 (X=CH$_2$; R=3-methyl-5-isoxazolyl): (Reference Example 10) mp.: 138° to 139° C. Elemental Analysis (%) C$_{14}$H$_{14}$N$_3$O$_2$Cl Calculated: C, 57.64; H, 4.84; N, 14.40; Cl, 12.15 Found: C, 57.53; H, 4.82; N, 14.46; Cl, 12.37 NMR (CDCl$_3$) δ: 1.88 (4H, m), 2.42 (3H, s), 2.82 (2H, m), 2.95(2H, m), 6.90 (1H, s), 9.35 (1H, s), 9.57 (1H, br s, NH)

III2b-1 (X=O ; R=3-Isoxazolyl): (Reference Example 11) mp.: 180° to 181° C. Elemental Analysis (%) C$_{12}$H$_{10}$n$_3$O$_3$Cl Calculated: C, 51.53, H, 3.60; N, 15.02; Cl, 12.68 Found: C, 51.60; H, 3.60; N, 14.97; Cl, 12.93 NMR (CDCl$_3$) δ: 3.04 (2H, t, J=5.8 Hz), 4.06 (2H, t, J=5.8 Hz), 4.81 (2H, AB-q), 6.95 (1H, d, J=1.8 Hz), 8.57 (1H, d, J=1.8 Hz), 8.94 (1H, br s, NH), 9.47 (1H, s)

III2c-1 (X=—CH$_2$CH$_2$—; R=3-isoxazolyl): (Reference Example 12) mp.: 115° to 116° C. Elemental Analysis (%) C$_{14}$H$_{14}$N$_3$O$_2$Cl Calculated: C, 57.63; H, 4.83; N, 14.40; Cl, 12.15 Found: C, 57.93; H, 4.98; N, 14.38; Cl, 11.89 NMR (CDCl$_3$) δ: 1.63 to 1.76 (4H, m), 1.71 to 1.92 (2H, m), 3.03 to 3.13 (4H, m), 6.94 (1H, d, J=1.8 Hz), 8.56 (1H, d, J=1.8 Hz), 9.00 (1H, br s, NH), 9.31 (1H, s)

III2f-1 (X=S; R=3-isoxazolyl): (Reference Example 13) mp.: 155° to 156° C. Elemental Analysis (%) C$_{12}$H$_{10}$N$_3$O$_2$SCl Calculated: C, 48.73; H, 3.40; N, 14.20; S, 10.84; Cl, 11.98 Found: C, 48.58; H, 3.48; N, 14.22; S, 10.75; Cl, 11.99 NMR (CDCl$_3$) δ: 2.98 (2H, t, J=5.8 Hz), 3.29 (2H, t, J=5.8 Hz), 3.90 (2H, s), 6.95 (1H, d, J=1.8 Hz), 8.57 (1H, d, J=1.8 Hz), 8.98 (1H, br s, NH), 9.47 (1H, s)

III2f-2 (X=S; R=3-methyl-5-isoxazolyl): (Reference Example 14) mp.: 172° to 173° C. Elemental Analysis (%) C$_{13}$H$_{12}$N$_3$O$_2$SCl Calculated: C, 50.40; H, 3.90; N, 13.56; S, 10.35; Cl, 11.44 Found: C, 50.58; H, 4.01; N, 13.47; S, 10.35; Cl, 11.52 NMR (CDCl$_3$) δ: 2.42 (3H, s), 2.98 (2H, t, J=6.6 Hz), 3.29 (2H, t, J=6.6 Hz), 3.90 (2H, s), 6.92 (1H, s), 8.58 (1H, br s, NH), 9.44 (1H, s)

Reference Example 15 preparation of 4-chloro-3-(amino(3-isoxazolyl)-methylene-amino)-5,6,7,8-tetrahydroquinoline (III3a-1)

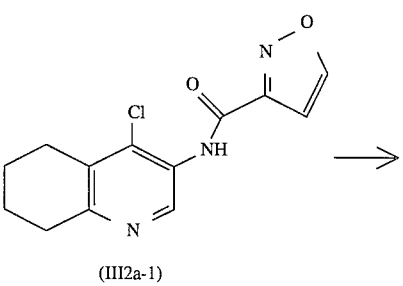

(III2a-1)

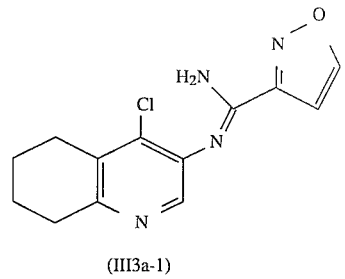

(III3a-1)

To 60 ml of methylene chloride are added 5.55 g of Compound (III2a-1) and 6.97 g of phosphorus pentachloride, and 1.60 g of pyridine is dropwise added. The resultant mixture is refluxed for 4.5 hours. To a previously chilled about 3.6N ammonia/isopropanol solution (140 ml) is added the above reaction mixture chilled with ice under keeping at temperature from −30° to −15° C. The temperature is raised to room temperature, and the mixture is stirred for 18 hours. The solvent is evaporated in vacuo, and the residue is mixed with 50 ml of ice water and 100 ml of methylene chloride and adjusted to pH 10 with conc. aqueous ammonia. The mixture is stirred at room temperature for 15 minutes and the methylene chloride layer is separated. The aqueous layer is further extracted with methylene chloride. The extract is washed with water, dried and concentrated for evaporation of the solvent to give 5.1 g of the titled compound (III3a-1) as crystals melting at 160° to 163° C. Yield: 92%. The crystals can be used for the subsequent reaction without purification, but a small portion is recrystallized from methylene chloride/isopropyl ether to give colorless crystals melting at 162° to 162° C. Elemental Analysis (%) C$_{13}$H$_{13}$N$_4$OCl Calculated: C, 56.42; H, 4.73; N, 20.24; Cl, 12.81 Found: C, 56.53; H, 4.91; N, 20.27; Cl, 12.72 NMR (CDCl$_3$) δ: 1.83 to 1.92 (4H, m), 2.78 to 2.86 (2H, m), 2.89 to 2.95 (2H, m), 5.38 (2H, br s, NH2), 6.98 (1H, d, J=1.6 Hz), 8.07 (1H, s), 8.49 (1H, d, J=1.6 Hz)

Reference Examples 16 to 20

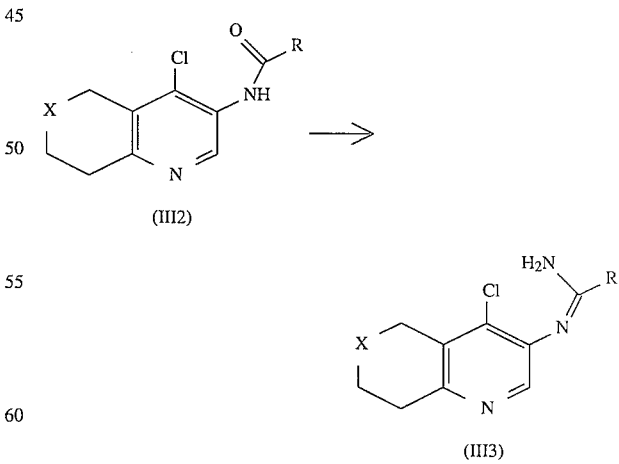

Using the corresponding isoxazolecarbonylamino derivatives (III2a), (III2b), (III2c), (III2f-1) and (III2f-2), the reaction is effected in the same manner as in Reference Example 15, whereby the following compounds are prepared.

III3a-2 (X=CH$_2$; R=3-methyl-5-isoxazolyl): (Reference Example 16) mp.: 206° to 208° C. Elemental Analysis (%) C$_{14}$H$_{15}$N$_4$OCl Calculated: C, 57.83; H, 5.20; N, 19.27; Cl, 12.20 Found: C, 57.80; H, 5.22; N, 19.16; Cl, 11.91 NMR (CDCl$_3$) δ: 1.84 (4H, m), 2.38 (3H, s), 2.83 (4H, m), 5.50 (2H, br s, NH2), 6.84 (1H, s), 8.02 (1H, s)

III3b-1 (X=O; R=3-isoxazolyl): (Reference Example 17) mp.: 195° to 196° C. Elemental Analysis (%) C$_{12}$H$_{11}$N$_4$O$_2$Cl Calculated: C, 51.71; H, 3.98; N, 20.10; Cl, 12.72 Found: C, 51.49; H, 4.03; N, 19.95; Cl, 12.66 NMR (CDCl$_3$) δ: 2.99 (2H, t, J=6.0 Hz), 4.04 (2H, t, J=6.0 Hz), 4.80 (2H, AB-q), 5.45 (2H, br s, NH2), 6.98 (1H, d, J=1.8 Hz), 8.15 (1H, s), 8.50 (1H, d, J=1.8 Hz)

III3c-1 (X=—CH$_2$CH$_2$—; R=3-isoxazolyl): (Reference Example 18) mp.: 197° to 199° C. Elemental Analysis (%) C$_{14}$H$_{15}$N$_4$OCl Calculated: C, 57.83; H, 5.19; N, 19.26; Cl, 12.19 Found: C, 57.57; H, 5.28; N, 19.11; Cl, 11.91 NMR (CDCl$_3$) δ: 1.63 to 1.93 (6H, m), 3.04 (3.09 (4H, m)), 5.41 (2H, br s, NH 2), 6.98 (1H, d, J=1.6 Hz), 7.96 (1H, s), 8.49 (1H, d, J=1.6 Hz)

III3f-1 (X=S; R=3-isoxazolyl): (Reference Example 19) mp.: 190° to 192° C. Elemental Analysis (%) C$_{12}$H$_{11}$N$_4$OSCl Calculated: C, 48.89; H, 3.76; N, 19.00; S, 10.87; Cl, 12.02 Found: C, 48.73; H, 3.75; N, 18.74; S, 10.85; Cl, 12.32 NMR (CDCl$_3$) δ: 2.97 (2H, t, J=6.2 Hz), 3.24 (2H, t, J=6.2 Hz), 3.92 (2H, s), 5.46 (2H, br s, NH2), 6.98 (1H, d, J=1.8 Hz), 8.13 (1H, s), 8.51 (1H, d, J=1.8 Hz)

III3f-2 (X=S; R=3-methyl-5-isoxazolyl): (Reference Example 20) mp.: 194° to 196° C. Elemental Analysis (%) C$_{13}$H$_{13}$N$_4$OSCl Calculated: C, 50.56; H, 4.24; N, 18.14 Found: C, 50.63; H, 4.13; N, 18.07 NMR (CDCl$_3$) δ: 2.39 (3H, s), 2.96 (2H, t, J=6.2 Hz), 3.22 (2H, t, J=6.2 Hz), 3.91 (2H, s), 5.36 (2H, br s, NH2), 6.85 (1H, s), 8.11 (1H, s)

EXAMPLE 37

2-(3-Isoxazolyl)-6,7,8,9-tetrahydro-1H-imidazo[4,5-c]-quinoline (Ia-7)

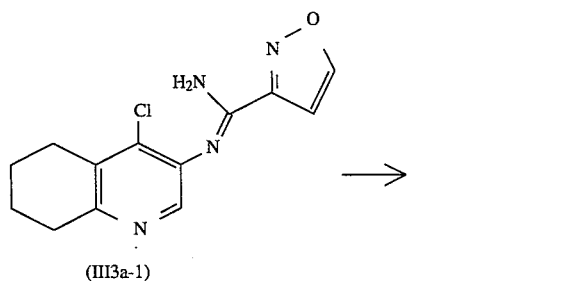

(III3a-1)

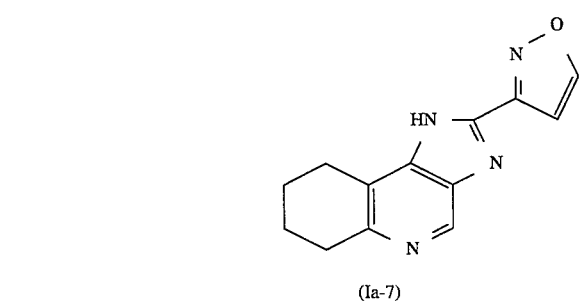

(Ia-7)

A mixture of 2.00 g of Compound (III3a-1) (obtained in Reference Example 15) and 18 ml of N-methyl-2-pyrrolidone is heated at 205° C. (bath temperature) for 1 hour. The solvent is evaporated in vacuo, and the residue is mixed with acetone and chilled. The precipitated crystals are filtered to give 1.83 g of Compound (Ia-7) hydrochloride. Yield: 91%. mp.: 263° to 267° C. (dec.). This product is recrystallized from methanol/isopropanol to give colorless crystals melting at 265° to 269° C. (dec.). Elemental Analysis (%) C$_{13}$H$_{13}$N$_4$OCl.1/2H$_2$O Calculated: C, 54.65; H, 4.94; N, 19.61; Cl, 12.41 Found: C, 54.64; H, 5.14; N, 19.67; Cl, 12.71

The above hydrochloride is converted into free base in a conventional manner to give the compound identified as Compound (Ia-7) obtained in Example 32.

EXAMPLES 38 to 42

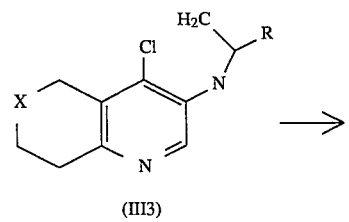

(III3)

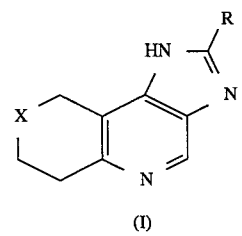

(I)

The reaction is effected in the same manner as in Example 37 to give Compound (Ia-6) (Example 38), Compound (Ib-7) (Example 39), Compound (Ic-6) (Example 40) and Compound (If-1) (Example 41) from Compound (III3a-2) (obtained in Reference Example 16), Compound (III3b-1) (obtained in Reference Example 17), Compound (III3c-1) (obtained in Reference Example 18) and Compound (III3f-1) (obtained in Reference Example 19), respectively. Physicochemical data of these compounds were identical with those of the compounds obtained in Examples 16, 25, 19 and 31, respectively.

Further, the reaction is effected in the same manner as in Example 37 to give 2-(3-methyl-5-isoxazolyl)-1,6,7,9-tetrahydroimidazo [4,5-d]thiopyrano[4,3-b]pyridine hydrochloride (If-2) (X=S; R=3-methyl-5-isoxazolyl, Example 42) from Compound (III3f-2) (obtained in Reference Example 20). mp.: 244° to 246° C. (dec.) Elemental Analysis (%) C$_{13}$H$_{13}$N$_4$OSCl Calculated: C, 50.56; H, 4.24; N, 18.14; S, 10.38; Cl, 11.48 Found: C, 50.39; H, 4.35 ; N, 17.85; S, 10.33; Cl, 11.37 NMR (d$_6$-DMSO) δ: 2.41 (3H, s), 3.12 (2H, t, J=5.6 Hz), 3.38 (2H, t, J=5.6 Hz), 4.25 (2H, s), 7.48 (1H, s), 9.35 (1H, s)

EXAMPLE 43

2-(3-Isoxazolyl)-8-oxo-1,6,7,9-tetrahydroimidazo[4,5-d]thiopyrano[4,3-b]pyridine (If-3)

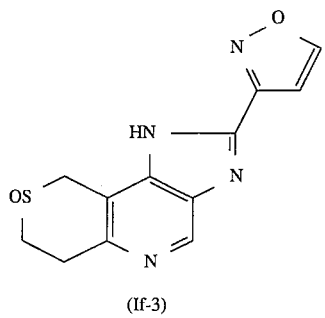

(If-3)

To a solution of 323 mg of Compound (If-1) in 30 ml of methanol is added a solution of 289 mg of sodium metaperiodate in 3 ml of water, and the resultant mixture is stirred at room temperature for 4 hours. The crystals in the reaction mixture are filtered off, and the filtrate is concentrated in vacuo. The residue is chromatographed on an alumina column, eluting with chloroform/methanol (15:1) to give 326 mg of Compound (If-3) as colorless crystals. Yield: 95%. The crystals are recrystallized from ethyl acetate/methanol to give Compound (If-3) as crystals melting at 210° to 212° C. (dec.) Elemental Analysis (%) $C_{12}H_{10}N_4O_2S$ Calculated: C, 52.54; H, 3.67; N, 20.42; S, 11.68 Found: C, 52.45; H, 3.90; N, 20.18; S, 11.43 NMR ($d_6$-DMSO) δ: 3.16 to 3.42 (4H, m), 4.38 (2H, AB-q), 7.26 (1H, d, J=1.6 Hz), 8.87 (1H, s), 9.23 (1H, d, J=1.6 Hz)

EXAMPLE 44

2-(3-Isoxazolyl)-8,8-dioxo-1,6,7,9-tetrahydroimidazo-[4,5-d]thiopyrano[4,3-b]pyridine hydrochloride (If-4)

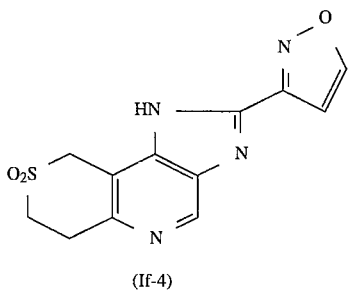

(If-4)

To a solution of 592 mg of Compound (III2f-1) (obtained in Reference Example 13) in 35 ml of methylene chloride is added 1.42 g of m-chloroperbenzoic acid under ice cooling, and the resultant mixture is stirred at room temperature for 6 hours. The reaction mixture is concentrated in vacuo, and the crystalline residue is washed well with isopropyl ether to give 670 mg of 4-chloro-3-(isoxazole-3-carbonylamino)-1,6,6-trioxo-7,8-dihydro-5H-thiopyrano[4,3-b]pyridine as crystals melting at 218° to 220° C. (dec.). Yield: 98%.

To a solution of 460 mg of the crystals in 92 ml of methylene chloride is dropwise added a solution of 0.26 ml of phosphorus tribromide in 0.3 ml of methylene chloride at temperature from −10° to −5° C., and the resultant mixture is stirred at temperature from 0° to 5° C. for 5 hours. The reaction mixture is mixed with ice water, neutralized with potassium carbonate and shaken with chloroform. The extract is dried and concentrated to remove the solvent. The residue is chromatographed on an alumina column, eluting with methylene chloride/isopropyl ether (30:1) to give 330 mg of 4-chloro-3-(isoxazolyl-3-carbonylamino)-6,6-dioxo-7,8-dihydro-5H-thiopyrano[4,3-b]pyridine as crystals melting at 200° to 202° C. Yield: 75%.

Using this compound, the reaction is effected in the same manner as in the method used for converting Compound (III2a-1) (obtained in Reference 9) into Compound (Ia-7), whereby Compound (If-4) is obtained. mp.: 199° to 202° C. Elemental Analysis (%) $C_{12}H_{11}N_4O_3SCl.H_2O$ Calculated: C, 41.80; H, 3.80; N, 16.25; S, 9.29; Cl, 10.28 Found: C, 41.53; H, 3.74; N, 16.16; S. 9.12; Cl, 9.99 NMR ($d_6$-DMSO) δ: 3.73 (4H, s), 4.93 (2H, s), 7.40 (1H, d, J=1.6 Hz), 9.33 (1H, d, J=1.6 Hz), 9.38 (1H, s)

EFFECT OF THE INVENTION

The compounds of the present invention show high affinity to cerebral benzodiazepine receptor, and are useful for treating various psychotropic disorders. The study of various drugs having an ability of binding to this receptor has revealed that these drugs can be classified in the following five groups according to their functions (aggressive or suppressive) and their potency (strong or weak) in the central nervous system: 1) Full agonist (central nerve inhibition, antianxiety, anticonvulsion), 2) partial agonist (selective antianxiety), 3) antagonist (antagonism to both aggressive and suppressive actions), 4) partial inverse agonist (central nervous acceleration, convulsion or recognition reinforcing activity, anesthesia antagonism), 5) full inverse agonist (induction of convulsion or anxiety). Further, it is also known that to which group a particular drug belongs can be determined by measuring the strength of inhibitory or reinforcing activity on the convulsion induced by the administration of pentylenetetrazole [C, Braestrup et al., Biochem. Pharmacol. 33, 859 (1984)]. It is pointed out by M. Sarter et al., TINS 11, 13 (1988), that a partial inverse agonist can be nootropic agent or cognition enhancer, in view of the fact that methyl β-carboline-3-carboxylic acid (β-CCM), a kind of inverse agonist, can reinforce the memorial and learning behavior of an animal, or that diazepam, a kind of agonist, inhibits human memory. Accordingly, of the compounds of the present invention, those showing agonist activity are expected to be useful as antianxiety agents or anticonvulsants, those showing antagonistic activity are expected to be useful as antagonists against overdosage of benzodiazepines, and those showing inverse agonist activity are expected to be useful as psychotropic agents, nootropic agents or anesthesia antagonists.

The compounds of the present invention were subjected to the following pharmacological experiments. The numbers of the test compounds listed in the tables correspond to those used in the foregoing Examples.

Experiment 1

Test on Binding to Benzodiazepine Receptor

This test was carried out modifying partially a method of Moehler & Okada, Science, 198, 849–851 (1977). Receptor preparation was provided from the cerebral cortex of male Wistar rats (11–13 weeks age). Inhibitory action of the test compound on the specific binding of tritium-labeled diazepam to the receptor was evaluated as follows: 2 nM tritium-labeled diazepam and an aqueous solution of the test compound in 5 or 6 different concentrations were incubated with the receptor preparation at 0° C. for 60 minutes. The 50% inhibitory concentration ($IC_{50}$) was measured by the concentration-response curve. In addition, the inhibitory constant (Ki) of the test compound was calculated by dissociation constant (Kd) and concentration (L) of tritium-labelled diazepam. Table 1 shows the experimental results.

$Ki = IC_{50} \div (1 + L/Kd)$

TABLE 1

| Test Compound | Ki (nM) |
|---|---|
| Ia-1 | 13.7 |
| Ia-3 | 1.90 |
| Ia-5 | 3.46 |
| Ia-6 | 2.19 |
| Ia-7 | 1.30 |
| Ib-5 | 6.97 |
| Ib-7 | 2.09 |
| Ic-3 | 6.06 |
| Ic-6 | 2.29 |
| Ic-7 | 9.47 |
| Id-1 | 2.55 |
| Id-2 | 8.94 |
| Ie-1 | 7.20 |
| If-1 | 0.44 |
| Ig-1 | 2.80 |

Experiment 2

Antagonism of Pentylenetetrazole-Induced Convulsion

Agonistic activity was evaluated in this Experiment. Pentylenetetrazole was subcutaneously administered male mice (a group of 8–16 male mice was employed in each test) at a dose of 125 mg/kg immediately after intravenous injection of the test compound. The dose ($ED_{50}$) required to prevent tonic convulsion and death in 50% of the animals during subsequent 2-hour observation period was calculated by the probit method. Table 2 shows the experimental results.

TABLE 2

| Test Compound | $ED_{50}$ (mg/kg) |
|---|---|
| Ia-1 | 7.85 |
| Ia-6 | 0.17 |
| Ib-5 | 0.80 |
| Ic-7 | 1.05 |
| Id-2 | 0.74 |
| Ig-1 | 3.69 |

Experiment 3

Potentiation of Pentylenetetrazole-Induced Convulsion

Inverse agonist activity was evaluated in this Experiment. Pentylenetetrazole was subscutaneously administered male mice (a group of 8–16 male mice was employed in each test) at a dose of 90 mg/kg immediately after intravenous injection of the test compound. The dose ($ED_{50}$) required to produce tonic convulsion and death in 50% of the animals during subsequent 2-hour observation period was calculated by the probit method. Table 3 shows the experimental results.

TABLE 3

| Test Compound | $ED_{50}$ (mg/kg) |
|---|---|
| Ib-7 | 1.27 |
| Id-1 | 0.40 |
| Ie-1 | 0.25 |
| If-1 | 0.96 |

As shown above, the compounds of the present invention show high affinity to benzodiazepine receptor and exhibit inhibitory or accelerating activity to central nervous system.

What is claimed is:

1. A compound of the formula (I):

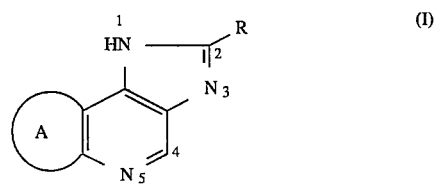

wherein

R is (a) phenyl or (b) a 5 membered aromatic heterocyclic group containing up to 3 hetero ring atoms selected from the group consisting of oxygen, sulfur and nitrogen, said groups (a) and (b) being unsubstituted or substituted by at least one substituent selected from the group consisting of alkyl, hydroxy, alkoxy, carboxy, alkoxycarbonyl, aralkoxycarbonyl, cyano, amino, mono- or di-(substituted) amino, hydrazine, hydroxyamino, alkoxyamino, halogen, nitro, formyl, alkanoyl, aroyl, (thio)carbamoyl, (thio)carbamoyloxy, (thio)ureido, sulfonamide, mono- or di-(substituted) sulfonamide, sulfonic acid, halogenoalkyl, hydroxyalkyl, alkoxyalkyl, acyloxyalkyl, nitroalkyl, (acyl)aminoalkyl, cyanoalkyl and carboxyalkyl, and A represents (1) a 5 or 7 membered alicyclic group or (2) a 5 or 7 membered alicyclic group in which at least one of the carbon atoms is substituted by an alkyl group of 1 to 10 carbon atoms, or a pharmaceutically acceptable salt thereof.

2. A compound as claimed in claim 1 wherein R represents optionally substituted isoxazolyl.

3. A compound according to claim 1 wherein the substituent in the definition of R is selected from the group consisting of $C_1$–$C_6$ alkyl, $C_1$–$C_6$ alkoxy and halogen.

4. A compound according to claim 1 wherein R is a 5 membered aromatic heterocyclic group containing up to 3 hetero ring atoms selected from the group consisting of oxygen, sulfur and nitrogen, said group being unsubstituted or substituted by at least one substituent as defined in claim 1.

5. A pharmaceutical composition comprising an effective amount of a compound as claimed in claim 1 as an essential active ingredient together with a suitable carrier or excipient therefor.

* * * * *